US012773560B2

(12) United States Patent
Zhang et al.

(10) Patent No.: US 12,773,560 B2
(45) Date of Patent: *Oct. 27, 2026

(54) MEDICAL DEVICE AND METHOD FOR TACHYARRYTHMIA DETECTION

(71) Applicant: Medtronic, Inc., Minneapolis, MN (US)

(72) Inventors: Xusheng Zhang, Shoreview, MN (US); Kevin L. Dehmer, Rogers, MN (US); Saul E. Greenhut, Denver, CO (US); Troy E. Jackson, Rogers, MN (US); Yuanzhen Liu, Palo Alto, CA (US)

(73) Assignee: Medtronic, Inc., Minneapolis, MN (US)

( * ) Notice: Subject to any disclaimer, the term of this patent is extended or adjusted under 35 U.S.C. 154(b) by 419 days.

This patent is subject to a terminal disclaimer.

(21) Appl. No.: 18/491,670

(22) Filed: Oct. 20, 2023

(65) Prior Publication Data

US 2024/0042213 A1 Feb. 8, 2024

Related U.S. Application Data

(63) Continuation of application No. 17/087,960, filed on Nov. 3, 2020, now Pat. No. 11,801,385.

(60) Provisional application No. 62/932,012, filed on Nov. 7, 2019.

(51) Int. Cl.
*A61N 1/362* (2006.01)
*A61B 5/363* (2021.01)

(52) U.S. Cl.
CPC ............ *A61N 1/3621* (2013.01); *A61B 5/363* (2021.01)

(58) Field of Classification Search
CPC .... A61N 1/3621; A61N 1/3622; A61N 1/365; A61N 1/36592; A61N 1/39622; A61B 5/349; A61B 5/35; A61B 5/352; A61B 5/363
See application file for complete search history.

(56) References Cited

U.S. PATENT DOCUMENTS

| | | | |
|---|---|---|---|
| 5,086,772 | A | 2/1992 | Larnard et al. |
| 5,330,507 | A | 7/1994 | Schwartz |
| 5,893,882 | A | 4/1999 | Peterson et al. |
| 5,978,700 | A | 11/1999 | Nigam |
| 6,208,899 | B1 | 3/2001 | Kroll |
| 7,031,771 | B2 | 4/2006 | Brown et al. |

(Continued)

FOREIGN PATENT DOCUMENTS

| | | |
|---|---|---|
| CN | 107257656 A | 10/2017 |
| CN | 108883279 A | 11/2018 |

OTHER PUBLICATIONS

Thomas Bruggeman et al., "Tachycardia Detection in Modern Implantable Cardioverter-Defibrillators", Herzschrittmachertherapie Elektrophysiologie, Aug. 30, 2016, vol. 27, No. 3, pp. 171-185.

(Continued)

*Primary Examiner* — Allen Porter

(57) ABSTRACT

A medical device is configured to determine time intervals between consecutive cardiac events sensed from a cardiac electrical signal, increase a value of a tachyarrhythmia interval count in response to each of the determine time intervals detected as a tachyarrhythmia interval. The device is further configured to detect normal sinus rhythm events and the decrease the value of the tachyarrhythmia interval count in response to a threshold number of detected normal sinus rhythm events.

22 Claims, 12 Drawing Sheets

(56) References Cited

U.S. PATENT DOCUMENTS

| | | | |
|---|---|---|---|
| 7,130,677 | B2 | 10/2006 | Brown et al. |
| 7,496,403 | B2 | 2/2009 | Cao et al. |
| 7,496,409 | B2 | 2/2009 | Greenhut et al. |
| 7,734,333 | B2 | 6/2010 | Ghanem et al. |
| 7,734,336 | B2 | 6/2010 | Ghanem et al. |
| 7,742,812 | B2 | 6/2010 | Ghanem et al. |
| 7,761,142 | B2 | 7/2010 | Ghanem et al. |
| 7,761,150 | B2 | 7/2010 | Ghanem et al. |
| 7,769,452 | B2 | 8/2010 | Ghanem et al. |
| 7,774,049 | B2 | 8/2010 | Ghanem et al. |
| 7,826,893 | B2 | 11/2010 | Cao et al. |
| 7,894,894 | B2 | 2/2011 | Stadler et al. |
| 7,904,153 | B2 | 3/2011 | Greenhut et al. |
| 7,907,993 | B2 | 3/2011 | Ghanem et al. |
| 7,937,135 | B2 | 5/2011 | Ghanem et al. |
| 7,941,214 | B2 | 5/2011 | Kleckner et al. |
| 7,991,471 | B2 | 8/2011 | Ghanem et al. |
| 8,050,751 | B2 | 11/2011 | Zhang et al. |
| 8,050,759 | B2 | 11/2011 | Stegemann et al. |
| 8,068,901 | B2 | 11/2011 | Ghanem et al. |
| 8,095,205 | B2 | 1/2012 | Bhunia |
| 8,095,206 | B2 | 1/2012 | Ghanem et al. |
| 8,145,307 | B2 | 3/2012 | Zhang et al. |
| 8,160,684 | B2 | 4/2012 | Ghanem et al. |
| 8,170,654 | B1 | 5/2012 | Zhang et al. |
| 8,271,073 | B2 | 9/2012 | Zhang et al. |
| 8,301,233 | B2 | 10/2012 | Zhang et al. |
| 8,306,618 | B2 | 11/2012 | Ghanem et al. |
| 8,435,185 | B2 | 5/2013 | Ghanem et al. |
| 8,521,275 | B2 | 8/2013 | Stadler et al. |
| 8,577,455 | B2 | 11/2013 | Mitrani et al. |
| 8,855,755 | B2 | 10/2014 | Zhang et al. |
| 9,022,962 | B2 | 5/2015 | Brown |
| 9,174,062 | B2 | 11/2015 | Stadler et al. |
| 9,375,181 | B2 | 6/2016 | Hemming et al. |
| 9,526,908 | B2 | 12/2016 | Zhang et al. |
| 9,561,005 | B2 | 2/2017 | Zhang |
| 9,566,012 | B2 | 2/2017 | Greenhut et al. |
| 9,586,051 | B2 | 3/2017 | Greenhut et al. |
| 9,597,525 | B2 | 3/2017 | Cao et al. |
| 9,872,630 | B2 | 1/2018 | Stadler et al. |
| 9,956,423 | B2 | 5/2018 | Zhang et al. |
| 10,130,818 | B2 | 11/2018 | Greenhut et al. |
| 10,188,867 | B2 | 1/2019 | Zhang |
| 10,252,071 | B2 | 4/2019 | Cao et al. |
| 10,265,536 | B2 | 4/2019 | Stadler et al. |
| 10,328,274 | B2 | 6/2019 | Zhang et al. |
| 10,376,705 | B2 | 8/2019 | Zhang et al. |
| 10,406,373 | B2 | 9/2019 | Zhang |
| 10,470,681 | B2 | 11/2019 | Greenhut et al. |
| 10,493,291 | B2 | 12/2019 | Cao et al. |
| 10,507,332 | B2 | 12/2019 | Zhang et al. |
| 10,555,684 | B2 | 2/2020 | Zhang et al. |
| 10,561,332 | B2 | 2/2020 | Zhang et al. |
| 10,576,288 | B2 | 3/2020 | Cao et al. |
| 10,583,306 | B2 | 3/2020 | Zhang et al. |
| 10,799,710 | B2 | 10/2020 | Cao et al. |
| 2010/0331904 | A1 | 12/2010 | Warren et al. |
| 2011/0270335 | A1 | 11/2011 | Stadler et al. |
| 2016/0158567 | A1 | 6/2016 | Marshall et al. |
| 2017/0043173 | A1 | 2/2017 | Sharma et al. |
| 2017/0281034 | A1 | 10/2017 | Higgins et al. |
| 2017/0354827 | A1 | 12/2017 | Zhang et al. |
| 2018/0028085 | A1 | 2/2018 | Zhang et al. |
| 2018/0028828 | A1 | 2/2018 | Cao et al. |
| 2018/0207437 | A1 | 7/2018 | Zhang et al. |
| 2018/0303368 | A1 | 10/2018 | Zhang et al. |
| 2019/0029552 | A1 | 1/2019 | Perschbacher et al. |
| 2019/0111268 | A1 | 4/2019 | Christie et al. |
| 2019/0184164 | A1 | 6/2019 | Zhang et al. |
| 2019/0308026 | A1 | 10/2019 | Zhang et al. |
| 2019/0314637 | A1 | 10/2019 | Stadler et al. |
| 2019/0374783 | A1 | 12/2019 | Zhang et al. |
| 2020/0046988 | A1 | 2/2020 | Wilkinson et al. |
| 2020/0094065 | A1 | 3/2020 | Cao et al. |
| 2020/0114158 | A1 | 4/2020 | Zhang et al. |
| 2020/0170532 | A1 | 6/2020 | Zhang et al. |
| 2020/0178830 | A1 | 6/2020 | Zhang et al. |
| 2020/0197708 | A1 | 6/2020 | Cao et al. |

OTHER PUBLICATIONS

PCT International Search Report Completed Jan. 27, 2021, corresponding to counterpart, PCT Application No. PCT/US2020/058761, 4 pages.

PCT Written Opinion of the International Searching Authority Completed Jan. 27, 2021, corresponding to counterpart, PCT Application No. PCT/US2020/058761, 6 pages.

"Office Action Issued in Chinese Patent Application No. 202080077403.X", Mailed Date: Jun. 14, 2025, 7 Pages.

500

MEDICAL DEVICE AND METHOD FOR TACHYARRYTHMIA DETECTION

CROSS-REFERENCE TO RELATED APPLICATIONS

This application is a Continuation of U.S. patent application Ser. No. 17/087,960, filed Nov. 3, 2020, which claims the benefit of and priority to U.S. Provisional Patent Application Ser. No. 62/932,012 filed Nov. 7, 2019, the entire contents of which is incorporated herein by reference.

TECHNICAL FIELD

The disclosure relates generally to a medical device and method for detecting tachyarrhythmia using a medical device.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation (CV/DF) shocks to the heart upon detecting tachycardia or fibrillation.

The ICD may sense the cardiac electrical signals in a heart chamber and deliver electrical stimulation therapies to the heart chamber using electrodes carried by transvenous medical electrical leads. Cardiac signals sensed within a heart chamber generally have a high signal strength and quality for reliably sensing near-field cardiac electrical events, such as ventricular R-waves sensed from within a ventricle. In some proposed or available ICD systems, a non-transvenous lead may be coupled to the ICD, in which case cardiac signal sensing presents new challenges in accurately sensing cardiac electrical events from a sensing site outside the heart.

SUMMARY

In general, the disclosure is directed to techniques for detecting tachyarrhythmia and avoiding false tachyarrhythmia detection in the presence of cardiac signal amplitude variability and/or cardiac electrical signal noise, such as electromagnetic interference (EMI) or myopotential signals. A ventricular tachyarrhythmia detection, e.g., detection of ventricular tachycardia (VT) or ventricular fibrillation (VF), may be based on detecting a ventricular rate that is faster than a tachyarrhythmia detection rate for at least a predetermined number of ventricular cycles. The VT or VF rate may be detected by sensing R-waves from a cardiac electrical signal, determining ventricular intervals or RR intervals (RRIs) between consecutively sensed R-waves, and counting the number of ventricular intervals that are shorter than VT or VF detection intervals. Other cardiac events such as P-waves or T-waves and/or non-cardiac noise may be oversensed as ventricular R-waves due to cardiac signal amplitude variability and/or due to intervals of non-cardiac noise. Such oversensing may lead to increasing the count of VT or VF intervals when an underlying normal sinus rhythm (NSR) may be present. A medical device operating according to the techniques disclosed herein may detect NSR beats that are occurring during a series of ventricular intervals that includes tachyarrhythmia detection intervals. The device is configured to decrease a value of a tachyarrhythmia interval counter in response to detecting NSR beats that meet reset criteria. The tachyarrhythmia interval counter may be decreased to a predetermined value to prevent the value of a tachyarrhythmia interval counter from reaching a VT or VF detection threshold when an underlying NSR is present.

In one example, the disclosure provides a medical device including a cardiac electrical signal sensing circuit, a control circuit and a therapy delivery circuit. The cardiac electrical signal sensing circuit is configured to receive a cardiac electrical signal and sense cardiac events from the cardiac electrical signal. The control circuit is configured to determine time intervals between consecutive sensed cardiac events, detect tachyarrhythmia intervals from the determined time intervals, increase a value of a tachyarrhythmia interval count in response to detecting each of the detected tachyarrhythmia intervals, and detect a normal sinus rhythm interval from the determined time intervals. The control circuit determines when a reset threshold number of normal sinus rhythm intervals are detected and decreases the value of a tachyarrhythmia interval count in response to the reset threshold number of normal sinus rhythm intervals being detected. After decreasing the value of the tachyarrhythmia interval count, the control circuit determines when the tachyarrhythmia interval count subsequently reaches a tachyarrhythmia detection threshold and detects a tachyarrhythmia in response to the value of the tachyarrhythmia interval count reaching the tachyarrhythmia detection threshold. The therapy delivery circuit delivers a tachyarrhythmia therapy in response to the control circuit detecting the tachyarrhythmia.

In another example, the disclosure provides a method that includes sensing cardiac events from a cardiac electrical signal, determining time intervals between consecutively sensed cardiac events, detecting tachyarrhythmia intervals from the determined time intervals, increasing a value of a tachyarrhythmia interval count in response to detecting each of the detected tachyarrhythmia intervals, and detecting a normal sinus rhythm interval from the determined time intervals. The method further includes determining when a reset threshold number of normal sinus rhythm intervals are detected and decreasing the value of a tachyarrhythmia interval count in response to the reset threshold number of normal sinus rhythm intervals being detected. After decreasing the value of the tachyarrhythmia interval count, the method may further include determining that the tachyarrhythmia interval count subsequently reaches a tachyarrhythmia detection threshold value and detecting a tachyarrhythmia in response to the value of the tachyarrhythmia interval count reaching the tachyarrhythmia detection threshold. The method may include delivering a tachyarrhythmia therapy in response to detecting the tachyarrhythmia.

In another example, the disclosure provides a non-transitory computer-readable medium storing a set of instructions which, when executed by a control circuit of a medical device, cause the medical device to sense cardiac events from a cardiac electrical signal, determine time intervals between consecutively sensed cardiac events, detect tachyarrhythmia intervals from the determined time intervals, increase a value of a tachyarrhythmia interval count in response to detecting each of the detected tachyarrhythmia intervals, determine when a reset threshold number of normal sinus rhythm intervals are detected, and decrease the value of a tachyarrhythmia interval count in response to the reset threshold number of normal sinus rhythm intervals being detected. After decreasing the value of the tachyarrhythmia interval count, the instructions may further cause the device to determine that the tachyarrhythmia interval count subsequently reaches a tachyarrhythmia detection threshold value, detect a tachyarrhythmia in response to the value of the tachyarrhythmia interval count reaching the tachyarrhythmia detection threshold, and deliver a tachyarrhythmia therapy in response to detecting the tachyarrhythmia.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
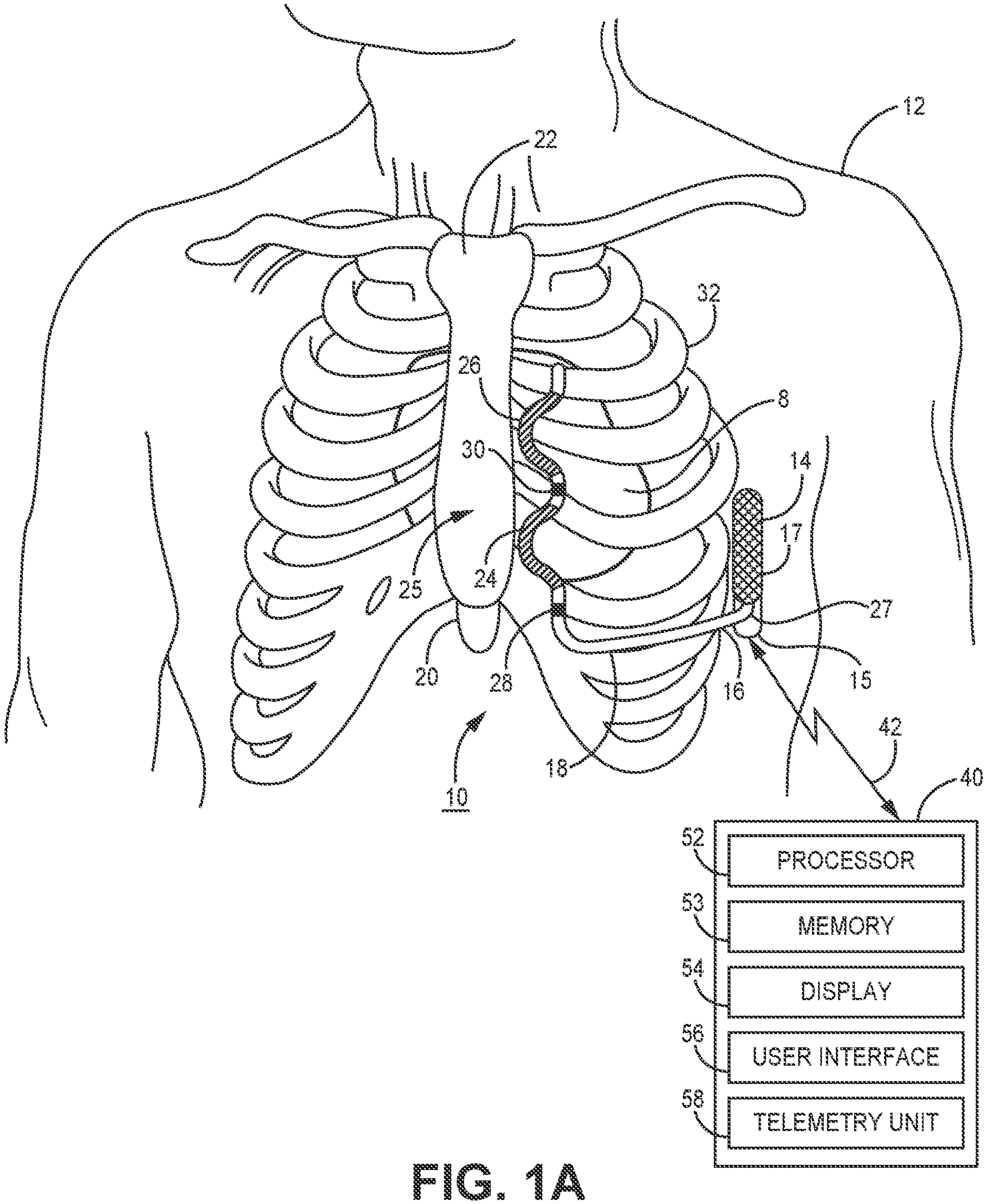
FIGS. 1A and 1B are conceptual diagrams of an extra-cardiovascular ICD system configured to sense cardiac electrical events and deliver cardiac electrical stimulation therapies according to one example.

In general, this disclosure describes techniques for detecting tachyarrhythmia by a medical device. A medical device may be configured to sense R-waves attendant to ventricular depolarizations from a cardiac electrical signal for use in controlling ventricular pacing and detecting ventricular tachyarrhythmias. A ventricular tachyarrhythmia may be detected in response to sensing a threshold number of R-waves occurring at time intervals, referred to as RRIs, that are less than a tachyarrhythmia detection interval. Cardiac events, such as P-waves or T-waves, and/or non-cardiac noise, such as EMI or myopotential signals, may be oversensed as R-waves, resulting in false RRIs being determined as ventricular tachyarrhythmia intervals. In some instances, variability in the R-wave signal strength due to patient motion or other factors may result in oversensing of cardiac events and/or non-cardiac noise, leading to relatively short RRIs being counted toward tachyarrhythmia detection when the underlying rhythm may actually be a normal sinus rhythm. False tachyarrhythmia detection may lead to a CV/DF shock or other tachyarrhythmia therapy delivered by the medical device, such as anti-tachyarrhythmia pacing (ATP), when such a therapy may not be needed.

A medical device performing the techniques disclosed herein detects NSR (or non-tachyarrhythmia) beats when a count of tachyarrhythmia intervals is non-zero and resets or adjusts the count of tachyarrhythmia intervals to a lower value in response to detecting the NSR beats. In this way, when incidents of NSR beats are detected, indicating the presence of an underlying normal sinus rhythm, detection of a tachyarrhythmia based on RRIs may be prolonged or all together inhibited by decreasing the value of a tachyarrhythmia interval counter one or more times as the counter is being incremented following each tachyarrhythmia interval detection.

In some examples, the medical device performing the techniques disclosed herein may be included in an extra-cardiovascular ICD system. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. Patient positional changes or patient physical activity as well as other factors may lead to variation in the cardiac event signal amplitudes, e.g., P-wave amplitudes, R-wave amplitudes and T-wave amplitudes, in the signal sensed from an extra-cardiovascular location. The extra-cardiovascular sensed signals may be more susceptible to signal amplitude variability and noise contamination, e.g., due to myopotentials or environmental EMI, than intracardiac sensed signals. The techniques disclosed herein for adjusting a tachyarrhythmia interval counter value based on the detection of NSR beats may be applied to a cardiac electrical signal sensed using extra-cardiovascular electrodes, with no limitation intended. As described herein, an analysis of RRIs and cardiac electrical signal morphology is performed for detecting ventricular beats that are likely to be NSR beats.

Tachyarrhythmia detection techniques are described herein in conjunction with an ICD and an implantable extra-cardiovascular medical lead carrying sensing and therapy delivery electrodes, but aspects disclosed herein may be utilized in conjunction with other cardiac medical devices or systems. For example, the tachyarrhythmia detection techniques as described in conjunction with the accompanying drawings may be implemented in any implantable or external medical device enabled for sensing intrinsic cardiac electrical events from cardiac signals received from a patient's heart via sensing electrodes, including implantable pacemakers, ICDs or cardiac monitors coupled to transvenous, pericardial or epicardial leads carrying sensing and therapy delivery electrodes; leadless pacemakers, ICDs or cardiac monitors having housing-based sensing electrodes; and external or wearable pacemakers, defibrillators, or cardiac monitors coupled to external, surface or skin electrodes.

Furthermore, while the illustrative examples presented herein refer to the detection of ventricular tachyarrhythmia, the disclosed techniques may be implemented in a medical device configured to detect (and optionally treat) atrial tachyarrhythmia. In this case, an atrial tachyarrhythmia interval counter may be incremented when a PP interval occurring between consecutively sensed atrial P-waves is less than an atrial tachyarrhythmia detection interval. Cardiac electrical signals, which may be sensed from within or outside an atrial chamber, may be analyzed for detecting atrial NSR beats based on an analysis of PP intervals and P-wave morphology. A value of an atrial tachyarrhythmia interval counter may be decreased when atrial NSR beats are detected according to the methods disclosed herein.

Figure 1B:
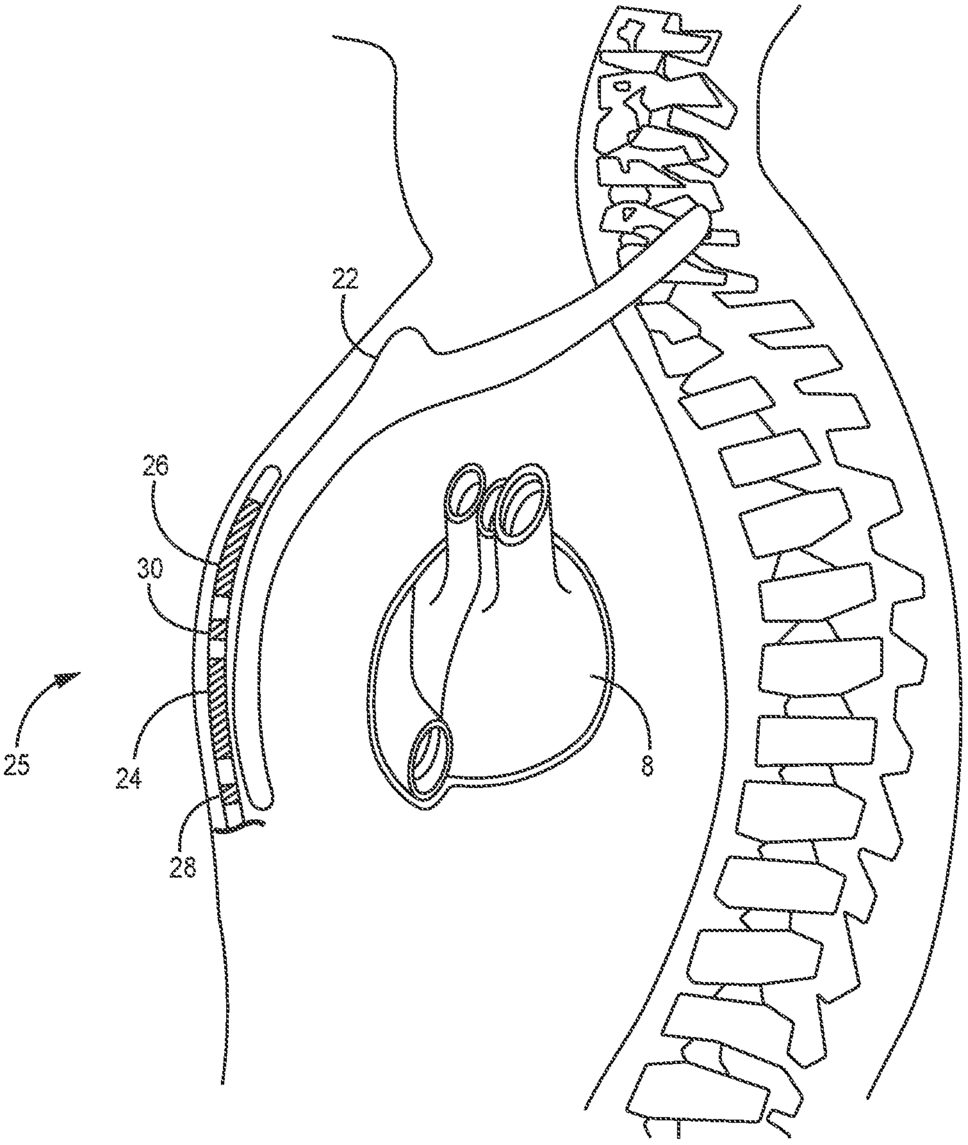

FIGS. 1A and 1B are conceptual diagrams of an extra-cardiovascular ICD system 10 configured to sense cardiac electrical events and deliver cardiac electrical stimulation therapies according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing high voltage CV/DF shocks, and in some examples cardiac pacing pulses, in response to detecting a cardiac tachyarrhythmia. However, the techniques disclosed herein for detecting tachyarrhythmia may be implemented in other cardiac devices configured for sensing cardiac events and determining the cardiac rate for controlling a cardiac electrical stimulation therapy.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both.

ICD 14 may obtain cardiac electrical signals corresponding to electrical activity of heart 8 via a combination of sensing electrode vectors that include combinations of electrodes 24, 26, 28 and/or 30. In some examples, housing 15 of ICD 14 is used in combination with one or more of electrodes 24, 26, 28 and/or 30 in a sensing electrode vector. Various sensing electrode vectors utilizing combinations of electrodes 24, 26, 28, and 30 and housing 15 are described below for sensing first and second cardiac electrical signals using respective first and second sensing electrode vectors that may be selected by sensing circuitry included in ICD 14.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals produced by the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design or electrode arrangement, however. In other examples, lead body 18 is a flexible elongated lead body without any pre-formed shape, bends or curves.

ICD 14 analyzes the cardiac electrical signals received from one or more sensing electrode vectors to monitor for abnormal rhythms, such as bradycardia, ventricular tachycardia (VT) or ventricular fibrillation (VF). ICD 14 may analyze the heart rate and morphology of the cardiac electrical signals to monitor for tachyarrhythmia in accordance with any of a number of tachyarrhythmia detection techniques. The tachyarrhythmia detection techniques may implement the aspects of the methods disclosed herein for detecting NSR beats and/or decreasing the value of a tachyarrhythmia interval counter to inhibit or prolong the process of detecting a tachyarrhythmia when NSR beats are detected.

ICD 14 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver anti-tachycardia pacing (ATP) in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space. FIGS. 1A and 1B are illustrative in nature and should not be considered limiting of the practice of the techniques disclosed herein.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as cardiac electrical signals retrieved from ICD 14.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling cardiac event sensing and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac signal sensing parameters, cardiac rhythm detection parameters and therapy control parameters used by ICD 14. At least some control parameters used in detecting cardiac events and tachyarrhythmia according to techniques disclosed herein may be programmed into ICD 14 using external device 40 in some examples.

Figure 2A:
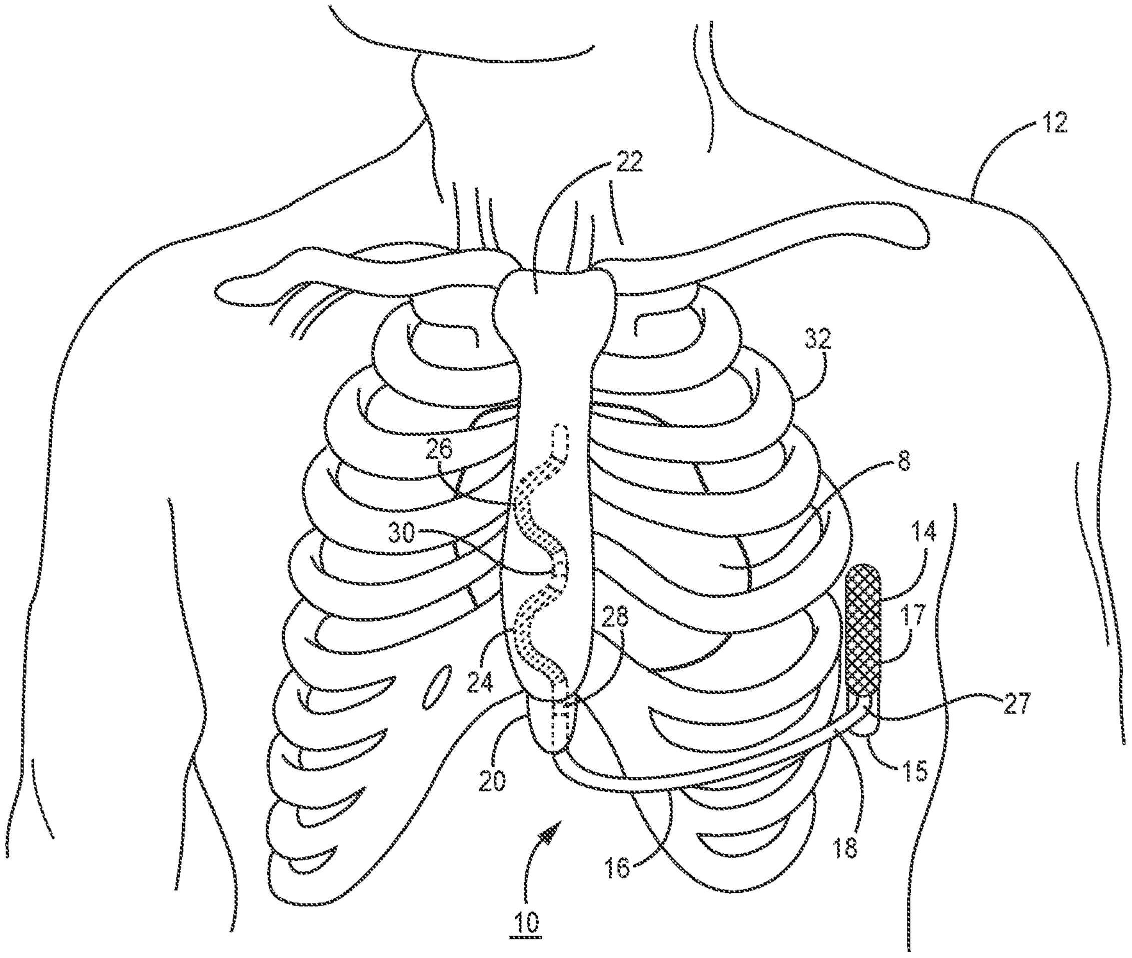
FIGS. 2A-2C are conceptual diagrams of a patient implanted with an extra-cardiovascular ICD system in a different implant configuration than the arrangement shown in FIGS. 1A-1B.
Figure 2B:
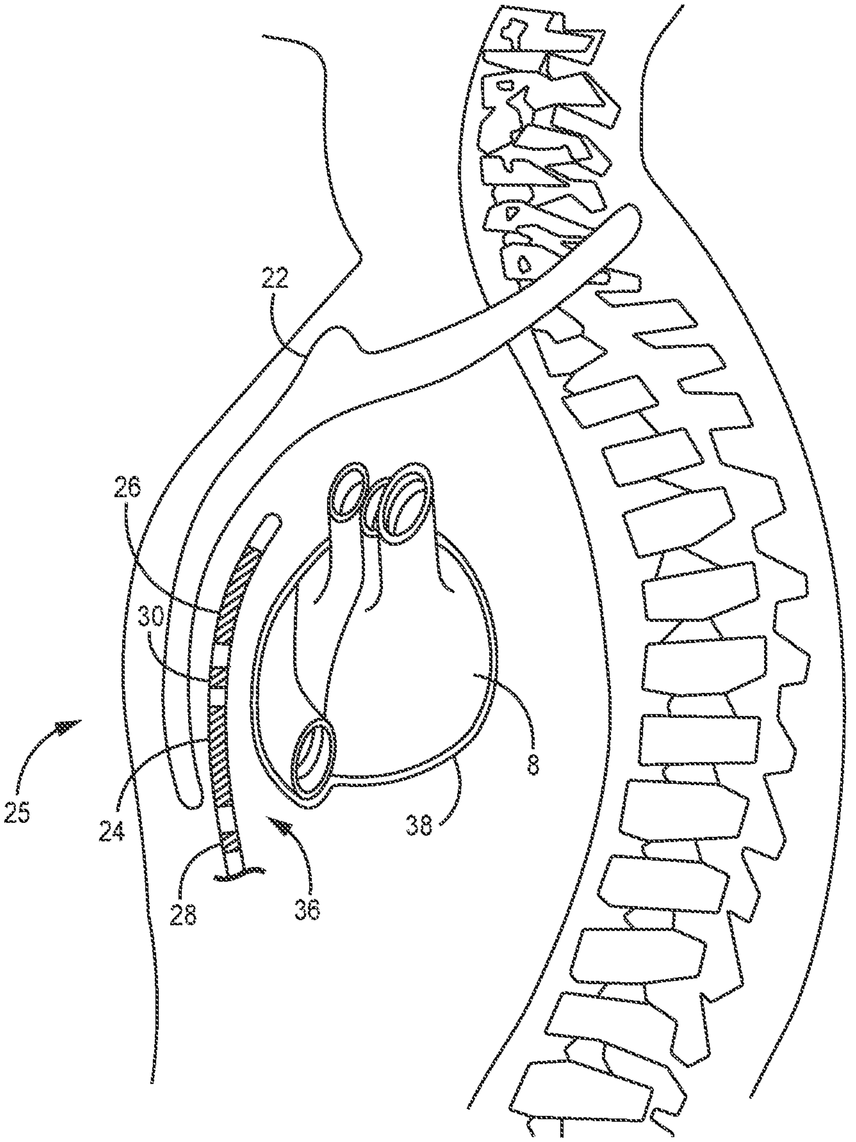
Figure 2C:
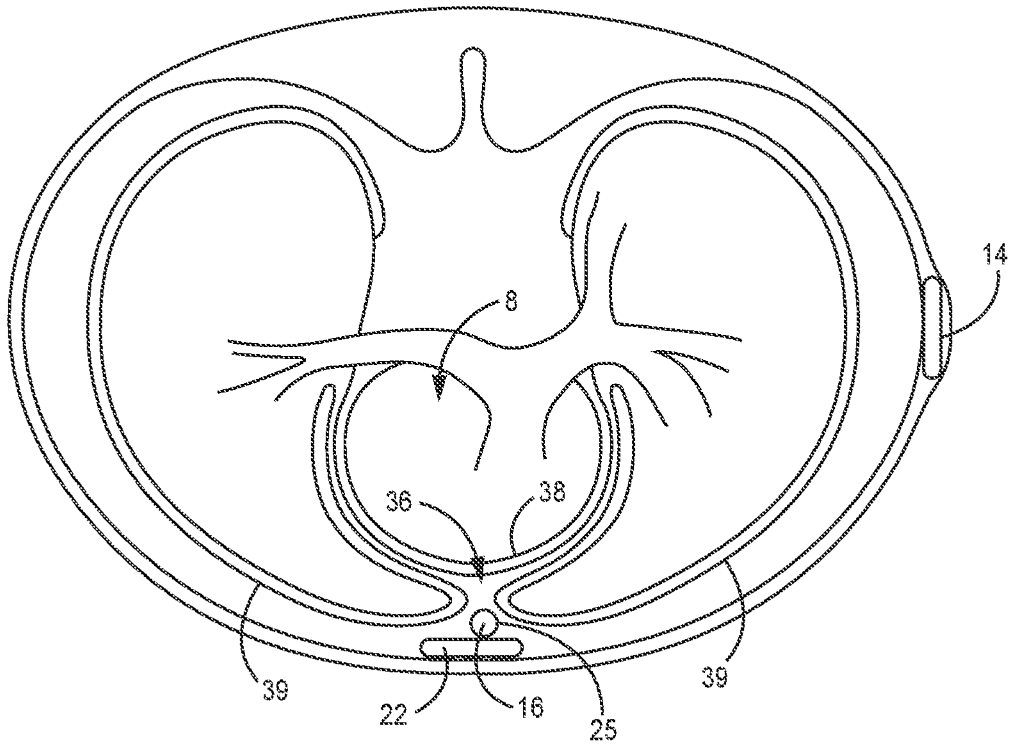

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8.

Figure 3:
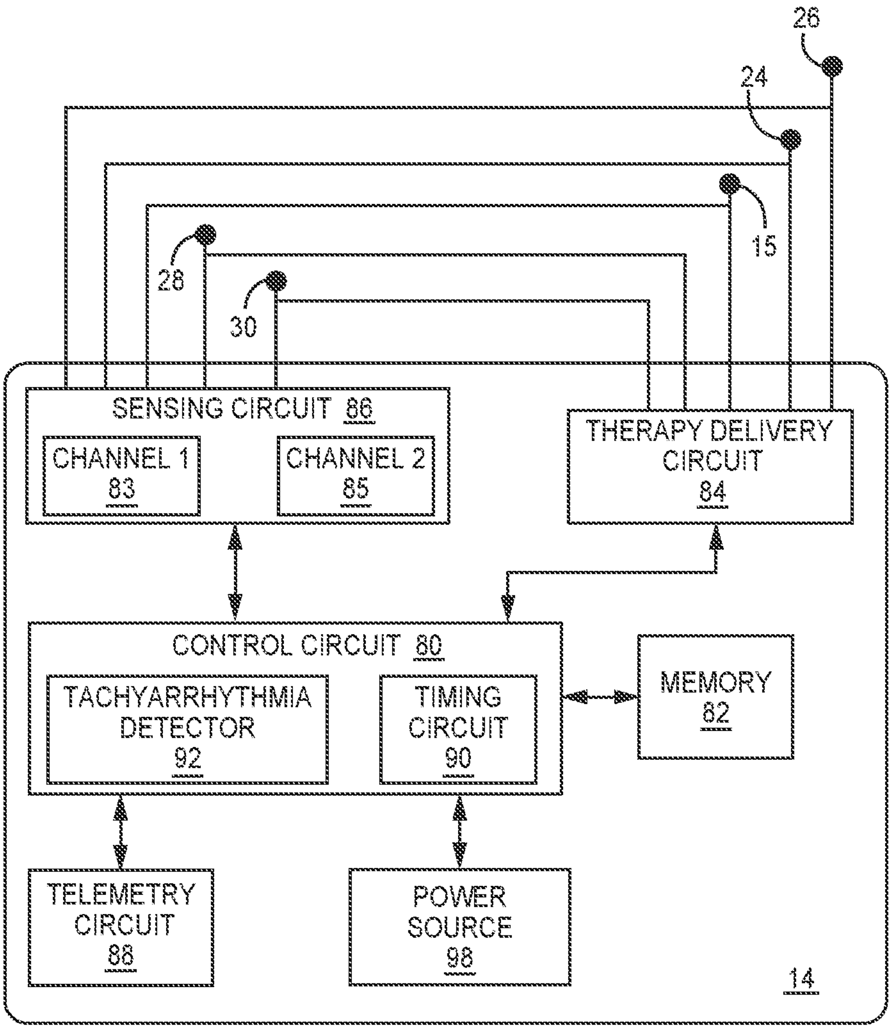
FIG. 3 is a conceptual diagram of an ICD according to one example.

FIG. 3 is a conceptual diagram of circuitry which may be included in ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 may be coupled to an extra-cardiovascular lead, such as lead 16 carrying extra-cardiovascular electrodes 24, 26, 28, and 30, for delivering electrical stimulation pulses to the patient's heart and for sensing cardiac electrical signals.

ICD 14 includes a control circuit 80, memory 82, therapy delivery circuit 84, cardiac electrical signal sensing circuit 86, and telemetry circuit 88. A power source 98 provides power to the circuitry of ICD 14, including each of the components 80, 82, 84, 86, and 88, as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol. Power source 98 is also coupled to components of cardiac electrical signal sensing circuit 86, such as sense amplifiers, analog-to-digital converters, switching circuitry, etc. as needed to perform the cardiac electrical signal sensing functionality of sensing circuit 86 as described herein.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac event sensing, detection of NSR beats and detection of tachyarrhythmia may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern implantable cardiac device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from at least two sensing electrode vectors from the available electrodes 24, 26, 28, 30, and housing 15. At least two cardiac electrical signals from two different sensing electrode vectors may be received simultaneously by sensing circuit 86 in some examples. Sensing circuit 86 may monitor one or both of the cardiac electrical signals simultaneously for sensing cardiac electrical events and/or producing digitized cardiac signal waveforms for analysis by control circuit 80. For example, sensing circuit 86 may include switching circuitry for selecting which of electrodes 24, 26, 28, 30, and housing 15 are coupled to a first sensing channel 83 and which electrodes are coupled to a second sensing channel 85 of sensing circuit 86.

Each sensing channel 83 and 85 may be configured to amplify, filter and digitize the cardiac electrical signal received from selected electrodes coupled to the respective sensing channel to improve the signal quality for detecting cardiac electrical events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIG. 4. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac event based on a sensing threshold crossing, first sensing channel 83 may produce a sensed event signal, such as an R-wave sensed event signal, that is passed to control circuit 80. The sensed event signal from the first sensing channel 83 is used by control circuit 80 to trigger storage of a time segment of the second cardiac electrical signal from second sensing channel 85 for processing and analysis for detecting NSR beats and adjusting a ventricular tachyarrhythmia interval counter as described below in conjunction with FIGS. 5 through 12. Memory 82 may be configured to store a predetermined number of cardiac electrical signal segments in circulating buffers under the control of control circuit 80, e.g., at least one, two, three or other number of cardiac electrical signal segments. Each segment may be written to memory 82 over a time interval extending before and after the triggering R-wave sensed event signal produced by the first sensing channel 83. Control circuit 80 may access stored cardiac electrical signal segments to confirm R-wave sensing by the first sensing channel 83 and appropriate tachyarrhythmia interval detections, which may precede satisfying tachyarrhythmia detection criteria and actual tachyarrhythmia detection.

The R-wave sensed event signals are also used by control circuit 80 for determining RRIs for detecting tachyarrhythmia and determining a need for therapy. An RRI is the time interval between consecutively sensed R-waves and may be determined between consecutive R-wave sensed event signals received from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

Control circuit 80 is also shown to include a tachyarrhythmia detector 92 configured to analyze signals received from sensing circuit 86 for detecting tachyarrhythmia episodes. Tachyarrhythmia detector 92 may be implemented in control circuit 80 as hardware, software and/or firmware that processes and analyzes signals received from sensing circuit 86 for detecting VT and/or VF. The timing of R-wave sense event signals received from sensing circuit 86 is used by timing circuit 90 to determine RRIs between consecutive sensed event signals. Tachyarrhythmia detector 92 may include comparators and counters for counting RRIs determined by timing circuit 92 that fall into various rate detection zones for determining a ventricular rate or performing other rate- or interval-based assessments for detecting and discriminating VT and VF.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter, and in some cases in a combined VT/VF interval counter, included in tachyarrhythmia detector 92. When an interval counter value reaches a detection threshold number of intervals, a ventricular tachyarrhythmia may be detected by tachyarrhythmia detector 92. Tachyarrhythmia detector 92 may be configured to perform other signal analysis for determining if other detection criteria are satisfied before detecting VT or VF, such as R-wave morphology criteria, onset criteria, and noise and oversensing rejection criteria. Furthermore, examples of parameters that may be determined by tachyarrhythmia detector 92 from cardiac electrical signals received from sensing circuit 86 for detecting NSR beats for use in adjusting the value of a VT or VF interval counter are described in conjunction with FIGS. 5-12.

To support these additional analyses, sensing circuit 86 may pass a digitized cardiac electrical signals, e.g., an electrocardiogram (ECG) signal, to control circuit 80 for morphology analysis performed by tachyarrhythmia detector 92. A cardiac electrical signal from the selected sensing vector, e.g., from first sensing channel 83 and/or the second sensing channel 85, may be passed through a filter and amplifier, provided to a multiplexer and thereafter converted to multi-bit digital signals by an analog-to-digital converter, all included in sensing circuit 86, for storage in memory 82. Memory 82 may include one or more circulating buffers to temporarily store digital cardiac electrical signal segments for analysis performed by control circuit 80. Control circuit 80 may be a microprocessor-based controller that employs digital signal analysis techniques to characterize the digitized signals stored in memory 82 to recognize and classify individual beats and the patient's heart rhythm employing any of numerous signal processing methodologies for analyzing cardiac signals and cardiac event waveforms, e.g., R-waves. As described below, processing and analysis of digitized signals may include determining signal features for detecting NSR beats and verifying that a tachyarrhythmia morphology is not present in cardiac electrical signal segments associated with VT/VF interval counts greater than a reset threshold. When the number of signal segments that meet tachyarrhythmia morphology detection criteria is less than a tachyarrhythmia morphology reset threshold, and the number of detected NSR beats meets an NSR reset threshold, the value of a VT and/or VF interval counter may be adjusted from its current value to a positive, lower, non-zero value in some examples. The VT and/or VF interval counter may be decreased to a prescribed value or by a prescribed decrement that is unequal to the number of NSR beats detected in some examples. In other examples, the value of the VT and/or VF interval counter(s) may be adjusted from its current value to 0.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when cardiac pacing pulses are delivered. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may control therapy delivery circuit 84 to deliver therapies such as ATP and/or CV/DF therapy. Therapy can be delivered by initiating charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape.

In some examples, the high voltage therapy circuit configured to deliver CV/DF shock pulses can be controlled by control circuit 80 to deliver pacing pulses, e.g., for delivering ATP, post shock pacing pulses or ventricular pacing pulses during atrioventricular conduction block or bradycardia. In other examples, therapy delivery circuit 84 may include a low voltage therapy circuit for generating and delivering pacing pulses for a variety of pacing needs.

It is recognized that the methods disclosed herein for detecting tachyarrhythmia may be implemented in a medical device that is used for monitoring cardiac electrical signals by sensing circuit 86 and control circuit 80 without having therapy delivery capabilities or in a medical device that monitors cardiac electrical signals and delivers cardiac pacing therapies by therapy delivery circuit 84, without high voltage therapy capabilities, such as cardioversion/defibrillation shock capabilities or vice versa. In some cases, the medical device may be configured to communicate with another medical device capable of delivering a therapy in response to a tachyarrhythmia detection.

Control parameters utilized by control circuit 80 for sensing cardiac events and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40.

Figure 4:
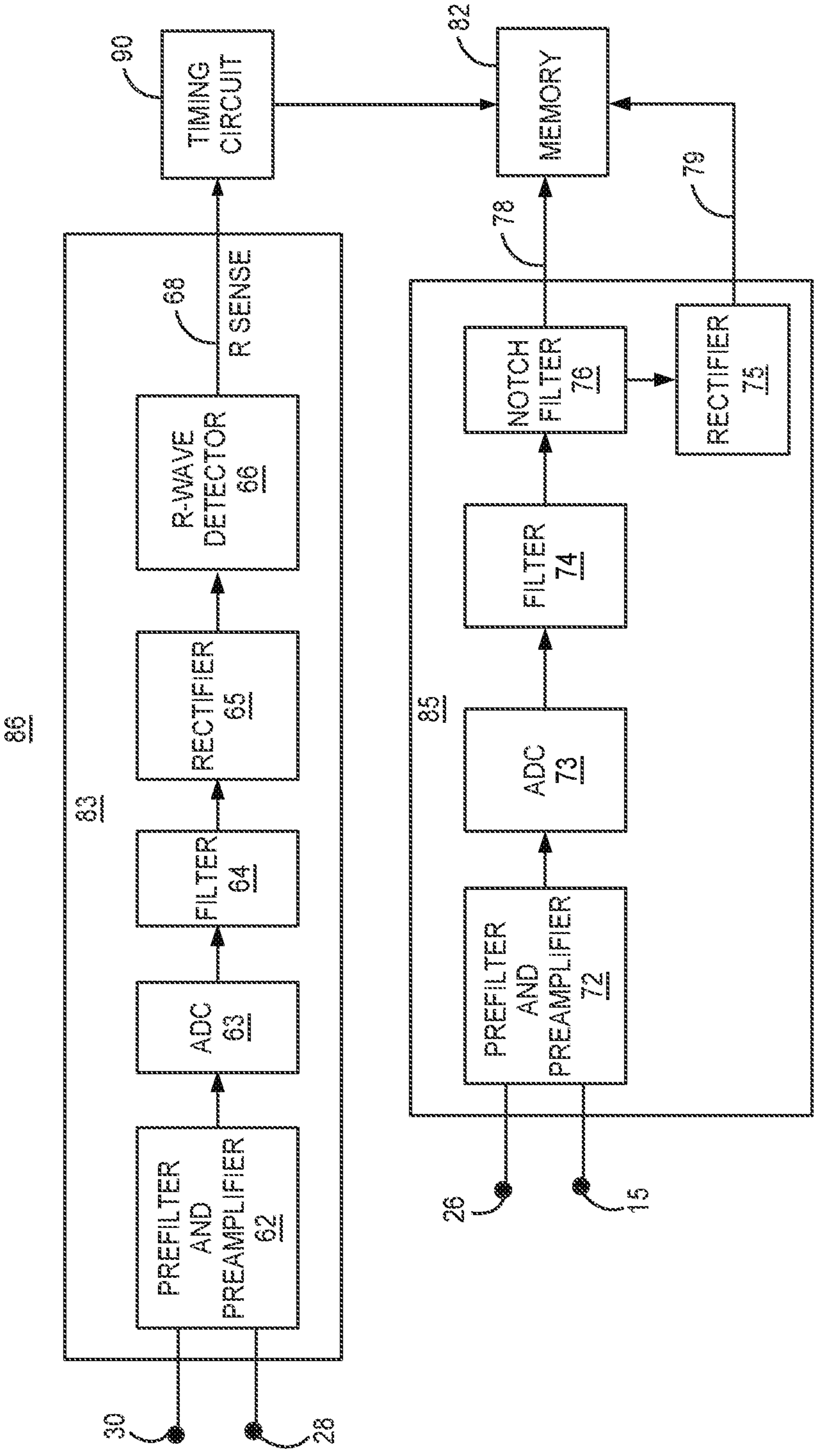
FIG. 4 is a diagram of circuitry that may be included in a sensing circuit of the ICD of FIG. 3.

FIG. 4 is a diagram of circuitry included in sensing circuit 86 having first sensing channel 83 and second sensing channel 85 according to one example. First sensing channel 83 may be selectively coupled via switching circuitry included in sensing circuit 86 to a first sensing electrode vector including at least one electrode carried by extra-cardiovascular lead 16 for receiving a first cardiac electrical signal. First sensing channel 83 may be coupled to a sensing electrode vector that is a short bipole, having a relatively shorter inter-electrode distance or spacing than the second electrode vector coupled to second sensing channel 85. First sensing channel 83 may be coupled to a sensing electrode vector that is approximately vertical (when the patient is in an upright position) or approximately aligned with the cardiac axis to increase the likelihood of a relatively high R-wave signal amplitude relative to P-wave signal amplitude. In one example, the first sensing electrode vector may include pace/sense electrodes 28 and 30, as shown. In other examples, the first sensing electrode vector coupled to sensing channel 83 may include a defibrillation electrode 24 and/or 26, e.g., a sensing electrode vector between pace/sense electrode 28 and defibrillation electrode 24 or between pace/sense electrode 30 and either of defibrillation electrodes 24 or 26. In still other examples, the first sensing electrode vector may be between defibrillation electrodes 24 and 26.

Sensing circuit 86 includes second sensing channel 85 that receives a second cardiac electrical signal from a second sensing vector, for example from a vector that includes one electrode 24, 26, 28 or 30 carried by lead 16 paired with housing 15. Second sensing channel 85 may be selectively coupled to other sensing electrode vectors, which may form a relatively longer bipole having an inter-electrode distance or spacing that is greater than the sensing electrode vector coupled to first sensing channel 83 in some examples. The second sensing electrode vector may be, but not necessarily, approximately orthogonal to the first channel sensing electrode vector in some cases. For instance, defibrillation electrode 26 and housing 15 may be coupled to second sensing channel 85, as shown, to provide the second cardiac electrical signal. As described below, the second cardiac electrical signal received by second sensing channel 85 via a long bipole may be used by control circuit 80 for analysis and detection NSR beats. The long bipole coupled to second sensing channel 85 may provide a relatively far-field or more global cardiac signal compared to the relatively shorter bipole coupled to the first sensing channel. The particular electrodes indicated as being coupled to first sensing channel 83 and second sensing channel 85 are shown as illustrative examples with no limitation intended. In other examples, any vector selected from the available electrodes, e.g., electrodes 24, 26, 28, 30 and/or housing 15, may be included in a sensing electrode vector coupled to the first and second sensing channels 83 and 85. The sensing electrode vectors coupled to first sensing channel 83 and second sensing channel 85 may be different sensing electrode vectors, which may have no common electrodes or only one common electrode but not both.

In other examples, the sensing electrode vectors may be the same sensing electrode vectors, however, the two sensing channels 83 and 85 may include different filters or other processing circuitry to facilitate different analysis, e.g., different signal feature determinations, of the two signals. For example, the first sensing channel may filter and process the received cardiac electrical signal for sensing a first signal for detecting R-waves in response to an R-wave sensing threshold crossing for determining RRIs. The second sensing channel 85 may filter and process the received cardiac electrical signal for sensing a second signal that is passed to control circuit 80 for determination and analysis of signal waveform morphology and specific morphological features for detecting NSR beats.

In the illustrative example shown in FIG. 4, the electrical signals developed across the first sensing electrode vector, e.g., electrodes 28 and 30, are received by first sensing channel 83 and electrical signals developed across the second sensing electrode vector, e.g., electrodes 26 and housing 15, are received by second sensing channel 85. The cardiac electrical signals are provided as differential input signals to the pre-filter and pre-amplifier 62 or 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

The digital outputs of ADC 63 and ADC 73 are each passed to respective filters 64 and 74, which may be digital bandpass filters. The bandpass filters 64 and 74 may have the same or different bandpass frequencies. For example, filter 64 may have a bandpass of approximately 13 Hz to 39 Hz for passing cardiac electrical signals such as R-waves typically occurring in this frequency range. Filter 74 of the second sensing channel 85 may have a bandpass of approximately 2.5 to 100 Hz. In some examples, second sensing channel 85 may further include a notch filter 76 to filter 60 Hz or 50 Hz noise signals.

The bandpass filtered signal in first sensing channel 83 is passed from filter 64 to rectifier 65 to produce a filtered, rectified signal. First sensing channel 83 includes an R-wave detector 66 for sensing cardiac events in response to the first cardiac electrical signal crossing an R-wave sensing threshold. R-wave detector 66 may include an auto-adjusting sense amplifier, comparator and/or other detection circuitry that compares the filtered and rectified cardiac electrical signal to an R-wave sensing threshold in real time and produces an R-wave sensed event signal 68 when the cardiac electrical signal crosses the R-wave sensing threshold outside of a post-sense blanking interval. The R-wave sensing threshold may be a multi-level sensing threshold as disclosed in commonly assigned U.S. Pat. No. 10,252,071 (Cao, et al.), incorporated herein by reference in its entirety. Briefly, the multi-level sensing threshold may have a starting sensing threshold value held for a time interval, which may be equal to a tachycardia detection interval or expected R-wave to T-wave interval, then drops to a second sensing threshold value held until a drop time interval expires. The sensing threshold drops to a minimum sensing threshold, which may correspond to a programmed sensitivity sometimes referred to as the "sensing floor," after the drop time interval. In other examples, the R-wave sensing threshold used by R-wave detector 66 may be set to a starting value based on the peak amplitude determined during the most recent post-sense blanking interval and decay linearly or exponentially over time until reaching a minimum sensing threshold. The techniques described herein are not limited to a specific behavior of the sensing threshold. Instead, other decaying, step-wise adjusted or other automatically adjusted sensing thresholds may be utilized.

The notch-filtered, digital cardiac electrical signal 78 from second sensing channel 85 may be passed to memory 82 for buffering segments of the second cardiac electrical signal 78 over predetermined time intervals in response to each of the R-wave sensed event signals 68 produced by the first sensing channel 83. In some examples, the buffered segment of the second cardiac electrical signal 78 is rectified by rectifier 75 before being stored in memory 82. In some cases, both the filtered, non-rectified signal 78 and the rectified signal 79 are passed to control circuit 80 and/or memory 82 for use in determining features of multiple segments of the second cardiac electrical signal, where each segment extends over a time interval that encompasses the time point of an R-wave sensed event signal produced by the first sensing channel 83, which triggers the storage of the signal segment in memory 82.

Control circuit 80 may buffer second cardiac electrical signal segments in memory 82 and retrieve stored signal segment from memory 82 for analysis when a threshold number of tachyarrhythmia intervals have been detected. Analysis of the second cardiac electrical signal segments may be performed for use in detecting NSR beats and for detecting tachyarrhythmia morphology signal segments as described herein. For instance, control circuit 80 may be configured to detect an NSR beat by determining an NSR morphology matching score and specific sensed event signal features from a second cardiac electrical signal segment corresponding to an R-wave that is sensed by the first sensing channel 83 at an RRI that is greater than an NSR interval threshold. When an NSR beat is detected based on the overall waveform morphology matching an NSR R-wave template and at least one specific waveform feature meeting an NSR threshold criterion, additional analysis may be performed to detect ventricular tachyarrhythmia morphology present in the time segment of the second cardiac electrical signal. Time segments of the notch-filtered, rectified signal 79 received from second sensing channel 85 may be used to detect each time segment having a ventricular tachyarrhythmia morphology. In some examples, when a first threshold number of NSR beats are detected and fewer than a second threshold number of ventricular tachyarrhythmia morphology signal segments are detected, the VT interval counter and/or VF interval counter may be reset to a lower value than its current value in order to inhibit or postpone a tachyarrhythmia detection. In this way, a false VT or VF detection due to intermittent or sustained oversensing of cardiac events or noise, particularly in the presence of varying R-wave amplitude (e.g., due to positional changes of the patient) is avoided when an underlying NSR is present.

The configuration of sensing channels 83 and 85 as shown in FIG. 4 is illustrative in nature and should not be considered limiting of the techniques described herein. The sensing channels 83 and 85 of sensing circuit 86 may include more or fewer components than illustrated and described in FIG. 4. For instance, in other examples a single sensing channel may be provided for sensing a cardiac electrical signal from which R-waves are sensed for producing R-wave sensed event signals and from which cardiac electrical signal segments may be analyzed for detecting an NSR morphology. In some examples, some components shown in FIG. 4 may be shared between sensing channels 83 and 85. For example, one or more of pre-filter and pre-amplifiers 62/72, ADC 63/73, and/or filters 64/74 may be shared components between sensing channels 83 and 85 with a single, sensed signal output split to two sensing channels for subsequent processing and analysis. Sensing circuit 86 and control circuit 80 include circuitry configured to perform the functionality attributed to ICD 14 in detecting tachyarrhythmias as disclosed herein.

Figure 5:
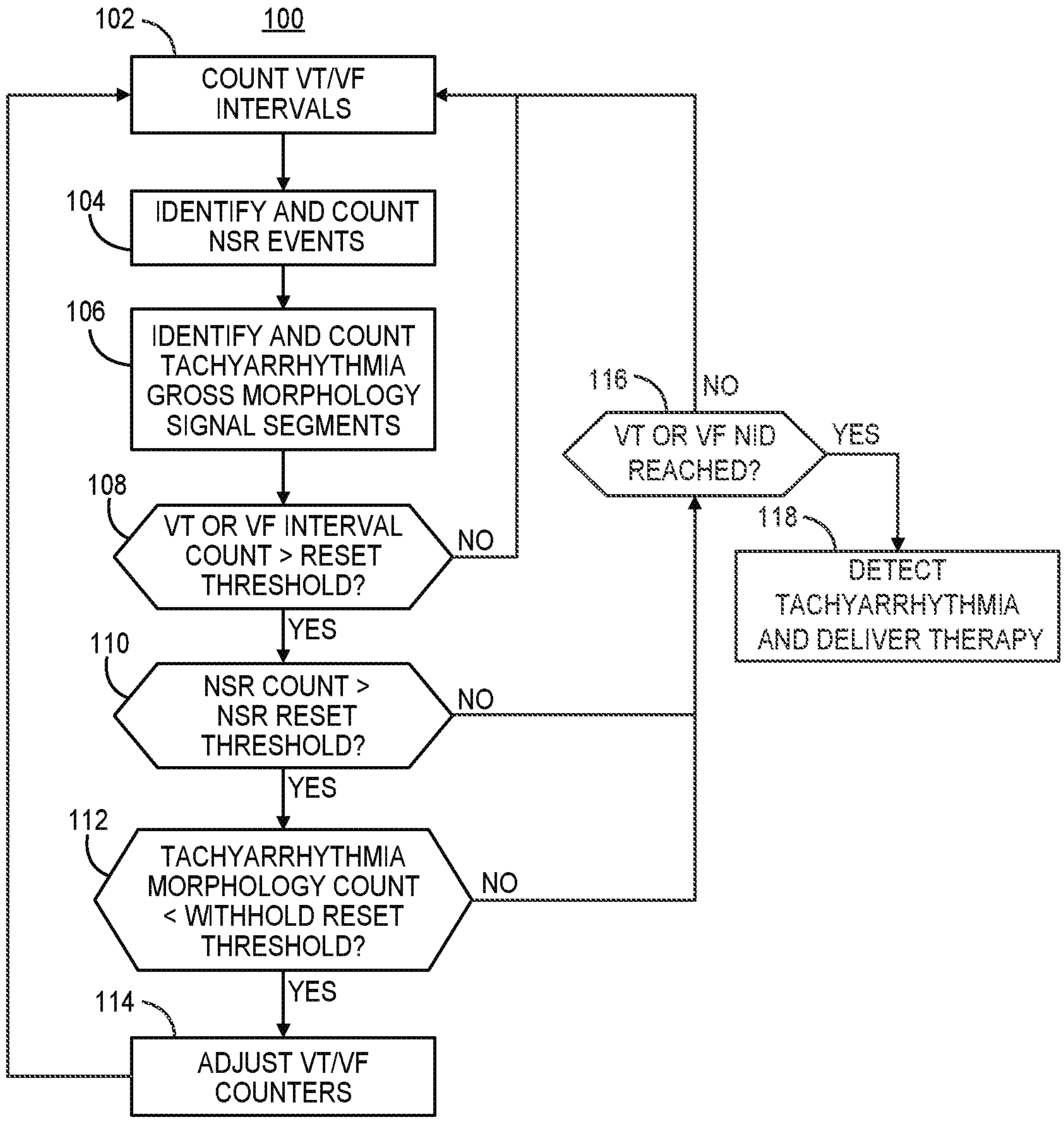
FIG. 5 is a flow chart of a method for controlling tachyarrhythmia interval counters according to one example.

FIG. 5 is a flow chart 100 of a method for controlling tachyarrhythmia interval counters in a tachyarrhythmia detection technique according to one example. In various examples presented herein, R-waves are sensed by the first sensing channel 83 of sensing circuit 86 based on R-wave sensing threshold crossings. RRIs are determined between pairs of consecutively sensed R-waves by timing circuit 90. These RRIs are compared to tachyarrhythmia detection intervals. When an RRI falls within a VT detection interval range, e.g., less than a VT detection interval threshold and greater than a VF detection interval threshold, and VT detection is enabled by a user, a VT interval counter value is increased at block 102. When an RRI is less than a VF detection interval threshold, a VF interval counter value is increased. In some cases, a combined VT/VF interval counter is increased in response to each RRI that is less than the VT detection interval threshold.

At block 104, control circuit 80 identifies and counts NSR events. In some examples, NSR events are identified and counted by identifying and counting NSR intervals. An NSR interval is an RRI that is greater than a NSR interval threshold. One method for establishing an NSR interval threshold is described below in conjunction with FIG. 6A. In other examples, identifying NSR events includes identifying an NSR beat morphology. An NSR beat morphology may be identified by analyzing a cardiac electrical signal segment over a beat morphology time interval encompassing the time of a sensed R-wave and determining that at least one morphology feature determined from the cardiac electrical signal segment over the beat morphology time interval meets NSR beat criteria. In some examples, an NSR interval may be identified and counted when at least one morphology feature that is determined from a cardiac electrical signal segment associated with the NSR interval meets NSR beat morphology criteria. The cardiac electrical signal segment meeting the NSR beat morphology criteria may be associated with the NSR interval by encompassing the time of a sensed R-wave associated with the NSR interval, e.g., ending the RRI identified as the NSR interval.

In order to detect VT or VF, the respective VT or VF interval counter is required to reach a number of intervals to detect (NID) the tachyarrhythmia. As an example, the NID to detect VT may require that the VT interval counter reaches 32 VT intervals counted out of the most recent 32 consecutive RRIs. The NID to detect VF may be programmed to 18 VF intervals out of the most recent 24 consecutive RRIs in one example or to 30 VF intervals out 40 consecutive RRIs in another example. When the VF interval counter reaches the required NID over a specified number of most recent RRIs, VF may be detected. In other examples, the NID may be programmable and range from as low as 12 to as high as 40, with no limitation intended, VT or VF intervals detected consecutively or non-consecutively out of a predetermined number of most recent RRIs. In some cases, a combined VT/VF interval counter may count both VT and VF intervals and detect a tachyarrhythmia episode based on the fastest intervals detected when a specified NID is reached. Intermittent episodes of oversensing due to incidences of noise or R-wave amplitude variability may be more likely to occur when the NID is programmed relatively high, e.g., 30 VF intervals out of 40 consecutive RRIs, than when the programmed NID is relatively lower. As a result, short runs of false tachyarrhythmia intervals may accumulate over the relatively high number of consecutive RRIs, potentially leading to a false VF detection. Accordingly, cardiac events that are highly likely to be NSR events based on RRIs and/or NSR morphology features are identified during tachyarrhythmia interval counting for prolonging or delaying tachyarrhythmia detection by decreasing the tachyarrhythmia interval counter(s) in response to the detected NSR events.

The NSR event criteria applied at block 104 for identifying and counting an NSR event may require that an R-wave sensed at an RRI is greater than an NSR interval threshold, that the RRI identified to be greater than the NSR interval threshold is stable compared to other RRIs identified to be greater than the NSR interval threshold (low variability or differences from one another), and/or that the R-wave occurs during an episode of multiple consecutive RRIs that are stable and greater than an NSR interval threshold. Additionally or alternatively, NSR event criteria may be applied to one or more cardiac electrical signal waveform morphology features. For example, NSR event criteria may require an overall waveform morphology matching an NSR R-wave morphology template and/or one or more specific morphological features of a sensed R-wave, such as amplitude, polarity, polarity pattern, time of an absolute maximum peak, maximum slope, signal area, signal width, or any combination thereof, may be required to match a respective NSR R-wave reference value of the specific feature within a matching threshold range. In some examples, low variability of specific morphology features between beats occurring at RRIs greater than an NSR threshold interval may be required to meet NSR beat criteria.

As described below in conjunction with FIGS. 6A-9, control circuit 80 may, in one example, identify RRIs that are longer than an NSR interval threshold and determine if a segment of the second cardiac electrical signal corresponding to an R-wave sensed from the first cardiac electrical signal at the NSR interval meets NSR beat morphology criteria. When a currently sensed R-wave occurs at an RRI that is greater than the NSR threshold interval and has at least one morphological feature that meets NSR morphology criteria, an NSR event may be identified and counted at block 104. As described below in conjunction with FIGS. 7 and 8, the NSR morphology criteria may be applied to signal features determined from a relatively short time segment of the second cardiac electrical signal, comprising a time point at which an R-wave is sensed from the first cardiac electrical signal associated with a detected NSR interval, so as to characterize a feature of the R-wave signal. As mentioned previously, a second cardiac electrical signal is not necessarily required. A single cardiac electrical signal may be used for sensing an R-wave at an NSR interval and performing morphology analysis on a segment of the cardiac electrical signal encompassing the time of the sensed R-wave for detecting NSR morphology.

Control circuit 80 may additionally analyze a segment of the second cardiac electrical signal corresponding to each sensed R-wave at block 106 to identify and count segments presenting a gross morphology that has a high probability of being a ventricular tachyarrhythmia morphology. One or more gross morphology features may be determined from an analysis of sample points spanning a time segment of the second cardiac electrical signal segment, which may encompass the time point of an R-wave sensed event signal but extends beyond the expected R-wave width, earlier and/or later than the R-wave sensed event signal time point. The ventricular tachyarrhythmia morphology criteria applied at block 106 may be applied to morphology metrics determined from a relatively longer time segment of the second cardiac electrical signal than the relatively shorter time segment used to identify NSR beats at block 104. Both of the longer and shorter time segments are within one cardiac cycle and encompass the time of an R-wave sensed event signal. The relatively longer time segments of the second cardiac electrical signal evaluated at block 106 extend beyond the expected width of a sensed R-wave, so as to characterize the similarity of the second cardiac electrical signal segment to ventricular tachyarrhythmia waveforms, e.g., fibrillation waves which may have a sinewave like morphology. The gross morphology features determined at block 106 for detecting a tachyarrhythmia morphology may include an amplitude morphology metric and/or a signal width morphology metric, as examples. Methods for identifying a tachyarrhythmia gross morphology signal segment at block 106 are described below in conjunction with FIGS. 10 and 11. Gross morphology features that may be used for detecting a tachyarrhythmia morphology may include a maximum slope, a number of peaks, a total signal area, a pulse count, a low slope content, a normalized mean rectified amplitude or other morphology features. Examples of gross morphology features may include any signal feature or metric determined using sample points that span a time interval extending longer than an expected NSR R-wave width and correlated to a tachyarrhythmia waveform.

At blocks 104 and 106, control circuit 80 may determine one or more signal features from each one of multiple segments of the second cardiac electrical signal, where each segment corresponds to (e.g., is buffered in response to) a sensed event signal produced by the first sensing channel 83. The signal features may be compared to NSR beat criteria and/or ventricular tachyarrhythmia morphology criteria for identifying and counting NSR beats and ventricular tachyarrhythmia morphology signal segments, respectively. The second cardiac electrical signal may be a relatively far field or more global cardiac signal compared to the first cardiac electrical signal as described above and/filtered or processed differently to enhance the specificity and sensitivity of the morphological analysis for detecting NSR beats and ventricular tachyarrhythmia morphology signal segments. For example, the second cardiac electrical signal may be sensed using a sensing electrode vector having an interelectrode distance that is greater than the interelectrode distance of the first sensing electrode vector. Additionally or alternatively, the second cardiac electrical signal segment may be filtered by a relatively wider band pass and a notch filter for attenuating 50-60 Hz noise. A segment of the second cardiac electrical signal over a predetermined time interval may be buffered in memory 82. The predetermined time interval encompasses a time point at which a cardiac event, e.g., R-wave, was sensed from the first cardiac electrical signal.

For example, in response to each R-wave sensed event signal 68 received from the first sensing channel 83, control circuit 80 may buffer a time segment of the second cardiac electrical signal 78 from the second sensing channel 85 in memory 82. The time segment may extend from a time point earlier than the time of the R-wave sensing threshold crossing to a time point later than the R-wave sensing threshold crossing that caused the first sensing channel 83 to generate an R-wave sensed event signal 68. The time segment may be 300 to 500 ms in duration, e.g., 360 ms in duration, including sample points preceding and following the R-wave sensed event signal. For instance, a 360 ms segment may include 92 sample points when the sampling rate is 256 Hz with 24 of the sample points occurring after the R-wave sensed event signal that triggered the storage of the signal segment and 68 sample points extending from the R-wave sensed event signal earlier in time from the R-wave sensed event signal. The entire segment, e.g., all 92 sample points may be used in determining gross morphology metrics for identifying and counting ventricular tachyarrhythmia segments and a portion of the entire segment, e.g., 48 sample points including the time point of the sensed R-wave, may be used in determining beat features for identifying and counting NSR beats.

At block 108, control circuit 80 compares the value of a VT and/or VF interval counter to a reset threshold value that is less than the NID. When the VT or VF interval counter is less than or equal to a predetermined reset threshold value, control circuit 80 continues to count VT/VF intervals at block 102 and identify and count NSR beats and tachyarrhythmia morphology signal segments. In some examples, the reset threshold is a value of 6 VF intervals. Additionally or alternatively, when VT detection is enabled, a reset threshold value of 7 may be applied to a combined VT/VF interval counter. The NID for detecting VF may be a count of 30 VF intervals out of the most recent 40 RRIs, as an example. In this example, when the VF interval counter is at a value of 7 or higher, or the combined VT/VF interval counter is at a value of 8 or higher, resetting of at least the VF interval counter is enabled ("yes" branch of block 108) when NSR and tachyarrhythmia morphology reset criteria are also met. When VT detection is enabled, resetting of the VT interval counter and/or combined VT/VF interval counter may enabled when at least one tachyarrhythmia interval counter reaches a predetermined reset threshold at block 108.

When a tachyarrhythmia interval counter is greater than its respective reset threshold at block 108, control circuit 80 compares the number of detected NSR events counted to NSR reset criteria at block 110. In some examples, if the count of NSR events is less than an NSR reset threshold at block 110, control circuit 80 advances to block 116 to check if VT or VF detection criteria are met. For instance, if the VT NID is reached, the VF NID is reached, or a combined VT/VF NID is reached, VT or VF may be detected at block 118, and a therapy may be delivered, e.g., ATP and/or a cardioversion or defibrillation shock.

When the tachyarrhythmia detection criteria are unmet at block 116, the process returns to block 102 to continue updating the various VT, VF and/or combined VT/VF interval counters and identifying NSR events and tachyarrhythmia morphology segments. The NSR reset threshold may be set to at least 2 NSR events out of 8 consecutively sensed R-waves (or 8 consecutive RRIs), in one example. Control circuit 80 may determine that the reset threshold number of NSR events is reached in response to detecting an NSR beat morphology associated with each of the reset threshold number of NSR intervals.

The NSR reset criteria applied at block 110 may require that at least one NSR event of the requisite number of NSR events occurs within the most recent two of the 8 (or other predetermined number) consecutively sensed R-waves. Each NSR event may be detected based on an NSR interval being detected and/or an NSR beat morphology being detected. Accordingly, the NSR reset criteria may require a first threshold number of NSR events detected out of a first predetermined number of sensed R-waves and a second threshold number of NSR events detected out of a second predetermined number of sensed R-waves. The first threshold number of NSR events may be equal to or greater than the second threshold number of NSR events. The first predetermined number of sensed R-waves is greater than the second predetermined number of sensed R-waves. The first predetermined number of sensed R-waves may overlap or comprise the second predetermined number of sensed R-waves. For example, when two NSR events are required to be detected out of eight consecutively sensed R-waves, at least one of the two NSR events may be required to be detected out of the most recent two of the eight consecutively sensed R-waves.

In some examples, the threshold number of NSR events that are required may be set based on the programmed NID required to detect tachyarrhythmia. For example, when the NID is relatively high, a higher number of NSR events may be required to adjust the tachyarrhythmia interval counter(s) than when the NID is relatively lower. To illustrate, if the NID to detect VF is 30 VF intervals out of 40 consecutive RRIs, the NSR reset threshold number of NSR events may be at least 4 out of the most recent 16 sensed R-waves whereas if the NID is 18 VF intervals out of 30 consecutive RRIs, the NSR reset threshold may be 2 NSR events out of 8 sensed R-waves. Techniques for identifying NSR events and determining when the NSR event count meets an NSR reset threshold are described below in conjunction with FIGS. 7 through 9.

When the NSR event count meets the NSR reset criteria at block 110 (e.g., greater than or equal to an NSR reset threshold), control circuit 80 compares the value of the ventricular tachyarrhythmia morphology count to a withhold reset threshold value at block 112. When the number of signal segments identified as having a tachyarrhythmia morphology is greater than or equal to the withhold reset threshold value, control circuit 80 withholds resetting or adjusting the VT, VF and/or combined VT/VF interval counters. As an example, the withhold reset threshold value may be a tachyarrhythmia morphology count of 6 out of the most recent 8 sensed R-waves. When five or fewer cardiac signal segments have been identified as having a ventricular tachyarrhythmia morphology out of 8 cardiac signal segments, resetting of the VT, VF and or combined VT/VF interval counters is enabled or allowed. When six or more cardiac electrical signal segments have been identified and counted as having a tachyarrhythmia morphology, however, resetting of the tachyarrhythmia interval counters is withheld ("no" branch of block 112). When the number of tachyarrhythmia signal segments identified equals or exceeds the withhold reset threshold, an adjustment to the VT, VF and/or VT/VF interval counters based on detected NSR events is precluded. In this way, resetting a ventricular tachyarrhythmia interval counter is not performed when evidence of a true tachyarrhythmia is detected based on the gross morphology metrics. The segments identified as having a ventricular tachyarrhythmia morphology may be among the eight (or other predetermined number) second cardiac electrical signal segments over which the reset threshold number of NSR events are detected. For example, if two segments of the second cardiac electrical signal out of eight consecutive signal segments are identified as NSR beats based on NSR beat criteria and all six or at least a portion of the remaining signal segments of the eight consecutive signal segments are identified as having a tachyarrhythmia morphology, tachyarrhythmia interval counter adjustments are not performed ("no" branch of block 112). Before returning to block 102 to continue counting VT/VF intervals, control circuit 80 may determine if one of the VT, VF or VT/VF interval counters has reached its respective NID at block 116, If so, control circuit 80 may detect tachyarrhythmia, and therapy delivery circuit 84 may deliver VT or VF therapy at block 118 according to programmed tachyarrhythmia therapies.

When the NSR event count meets the NSR reset criteria and the tachyarrhythmia morphology count is less than the withhold reset threshold ("yes" branch of block 112), control circuit 80 may adjust one or more of the VT interval counter, VF interval counter and/or combined VT/VF interval counter at block 114. In one example, the VF interval counter is adjusted from the current value to a predetermined value, e.g., to a value of 3. As another example, the combined VT/VF interval counter may be adjusted from a current value to a value of the current VT interval counter and the adjusted value of the VF interval counter or to a predetermined value. When VT detection is enabled, the VT interval counter may be adjusted from a current value to predetermined value, e.g., to a value of 2. The adjustment performed at block 114 is always a decrease in the value of the respective counter. If the situation should arise that all reset criteria are met but one of the counters is at a value that is less than the predetermined reset value for that counter, the counter is not increased to the reset value. For example, the VF interval counter may be greater than the reset threshold, e.g., 8 or more, but the VT interval counter may be at a value of 1. The VF interval counter may be reset to a value of 3 and the VT interval counter may remain at 1. A combined VT/VF interval counter may be adjusted according to the currently adjusted VT and VF interval counter values, to a value of 4 in this example.

A tachyarrhythmia interval counter value that is greater than the reset threshold (as determined at block 108) may be decreased from its current value to a value that is at least zero or a value that is greater than zero and less than the reset threshold in some examples. In other examples, the tachyarrhythmia interval count value may be decreased from its current value to an adjusted value that is based on the current value of the tachyarrhythmia interval counter. For example, when the current value of the tachyarrhythmia interval counter is any value greater than 15, the value may be decreased to a scaled, predetermined value of 10 at block 114. When the current value is greater than a reset threshold of 8, but less than or equal to 15, the value may be decreased to a scaled, predetermined value of 3, as an example. As such, the decreased, reset value may be based on the current value of the tachyarrhythmia counter. In some examples, predetermined reset values are defined for different ranges of the current tachyarrhythmia interval counter value. In other examples, the reset value is set as a fraction or portion of the current tachyarrhythmia interval counter. For instance, the tachyarrhythmia interval counter may be decreased to a positive integer value at block 114 that is approximately one third, one half or other portion of the current value of the tachyarrhythmia interval counter.

In still other examples, the tachyarrhythmia counter(s) may be adjusted at block 114 by a decrement set to a predetermined value, which may be a fixed value or adjustable based on the programmed NID and/or the current value of the tachyarrhythmia interval counter. The decrease in the tachyarrhythmia interval counter may or may not be equal to the number of NSR events identified. For instance, if six out of eight second cardiac electrical signal segments are identified as NSR beats associated with NSR intervals, the tachyarrhythmia counter value may be decreased by six but not below a predetermined minimum value (e.g., not less than one). If the number of NSR beats identified is two, the tachyarrhythmia interval counter value may be decreased by two, but not below a predetermined minimum value. In other examples, the tachyarrhythmia counter may be decreased to a predetermined value, which may be zero or any positive value that is less than its current value.

After adjusting the VT/VF interval counters at block 114, control circuit 80 returns to block 102 to continue counting VT/VF intervals as they are detected. Control circuit 80 may adjust the VT/VF interval counters at block 114 one or more times in response to the reset criteria being met at blocks 108, 110 and 112. After decreasing the value of a tachyarrhythmia interval counter one or more times at block 114, control circuit 80 may subsequently determine at block 116 that a tachyarrhythmia interval counter reaches a tachyarrhythmia detection threshold value, e.g., a programmed NID, and detect a tachyarrhythmia at block 118 in response to the value of the tachyarrhythmia interval counter reaching the tachyarrhythmia detection threshold. Therapy delivery circuit 84 may deliver a tachyarrhythmia therapy at block 118 in response to control circuit 80 detecting the tachyarrhythmia.

As discussed above, it is to be understood that the techniques for adjusting VT and/or VF interval counters as described herein based on detecting NSR events and tachyarrhythmia morphology signal segments may be adapted for adjusting atrial tachyarrhythmia counters used in detecting atrial tachyarrhythmia. P-waves may be sensed by a sensing circuit in response to a cardiac signal crossing a P-wave sensing threshold and PP intervals may be determined and compared to one or more atrial tachyarrhythmia detection intervals for counting atrial tachyarrhythmia intervals. Various NSR beat criteria and tachyarrhythmia morphology criteria may be applied to a cardiac electrical signal for determining when reset criteria are met adjusting the atrial tachyarrhythmia interval counter.

Figure 6A:
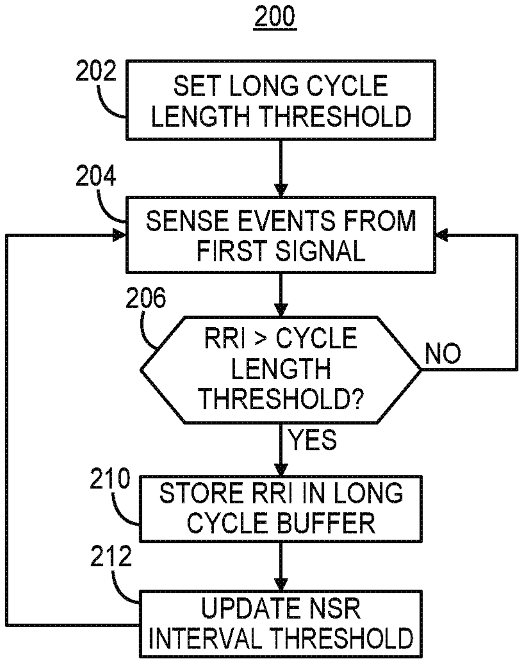
FIG. 6A is a flow chart of a method for setting an NSR interval threshold according to one example.

FIG. 6A is a flow chart 200 of a method for setting an NSR interval threshold according to one example. The NSR interval threshold may be used in identifying and counting NSR events, e.g., at block 104 of FIG. 5. At block 202, control circuit 80 sets a long cycle length threshold. The long cycle length threshold may be set based on a programmed ventricular tachyarrhythmia detection interval threshold. For example, the long cycle length threshold may be set to a predetermined interval longer than the longest tachyarrhythmia detection interval. When VF detection is enabled, but VT detection is not enabled, the long cycle length threshold may be set a predetermined interval greater than the VF detection interval threshold. The VF detection interval threshold may be set to 300 to 350 milliseconds (ms), as examples. For instance, if the VF detection interval is set to 320 ms, RRIs less than 320 ms are counted by the VF interval counter. The long cycle length threshold may be set 60 ms longer or to 380 ms.

When VT detection is enabled, the VT detection interval may be programmed to be in the range of 350 to 420 ms, or 400 ms as an example. In this case, the long cycle length threshold may be set to 60 ms longer than the VT detection interval, the longer of the VF and VT detection intervals. In the example of the VT interval being programmed to 400 ms, the long cycle length threshold may be set to 460 ms. After setting the long cycle length threshold at block 202, control circuit 80 may adjust the long cycle length threshold any time that the ventricular tachyarrhythmia detection parameters are reprogrammed by a user. For example, if VT detection becomes enabled or disabled or the VT detection interval threshold or VF detection interval threshold is reprogrammed to a different value, control circuit 80 may adjust the long cycle length threshold to a predetermined interval longer than the longest of the programmed ventricular tachyarrhythmia detection intervals for the enabled tachyarrhythmia detections.

At block 204, R-wave signals are sensed from the first cardiac electrical signal. RRIs are determined by control circuit 80 between consecutively received R-wave sensed event signals. VT, VF and/or combined VT/VF interval counters may be adjusted in response to detecting RRIs within a respective VT detection interval zone or VF detection interval zone as R-waves are sensed by the first sensing channel 83 (see FIG. 4). At block 206, control circuit 80 compares each RRI to the long cycle length threshold. When the RRI is longer than the long cycle length threshold, the RRI is stored in a long cycle length buffer at block 210. Memory 82 may be configured to have a first-in-first-out buffer for storing a predetermined number of long cycle lengths. In various examples, up to 8 to 12 long cycle lengths may be stored in the buffer. A newly detected long cycle length may overwrite the oldest long cycle length stored in the buffer. In one example, 11 long cycle lengths are stored in the long cycle length buffer of memory 82. If the RRI is not longer than the cycle length threshold at block 206, the process may return to block 204 to sense the next R-wave.

At block 212, an NSR interval threshold is updated based on the long cycle lengths stored in the long cycle length buffer. The NSR interval threshold may be set based on a mean, median, mode, range or other statistical parameter of the buffered long cycle lengths. Before updating the NSR interval threshold at block 212, one or more of the stored long cycle lengths may be rejected as outliers, a narrower range of the long cycle lengths buffered in memory 82 may be selected, or other subset of the stored long cycle lengths may be selected for use in setting the NSR interval threshold. In one example, the median value of the oldest 9 long cycle lengths stored in the long cycle length buffer are used to set the NSR interval threshold at block 212. The NSR interval threshold may be set to a fraction or percentage of the median value. In one example, the NSR interval is set to 75% of the median value of the oldest 9 long cycle lengths stored in a buffer that stores up to 11 long cycle lengths.

This process of storing long cycle lengths and updating the NSR interval threshold may be performed once a day or at more or less frequent scheduled intervals. In other examples, this process of storing long cycle lengths and updating the NSR interval threshold may be performed on a beat-by-beat basis, with each long cycle length detected being used to update the long cycle length buffer on a first-in-first out basis. The NSR interval threshold may be updated each time the long cycle length buffer is updated. In other examples the NSR interval threshold may be set to a fixed, predetermined value.

Figure 6B:
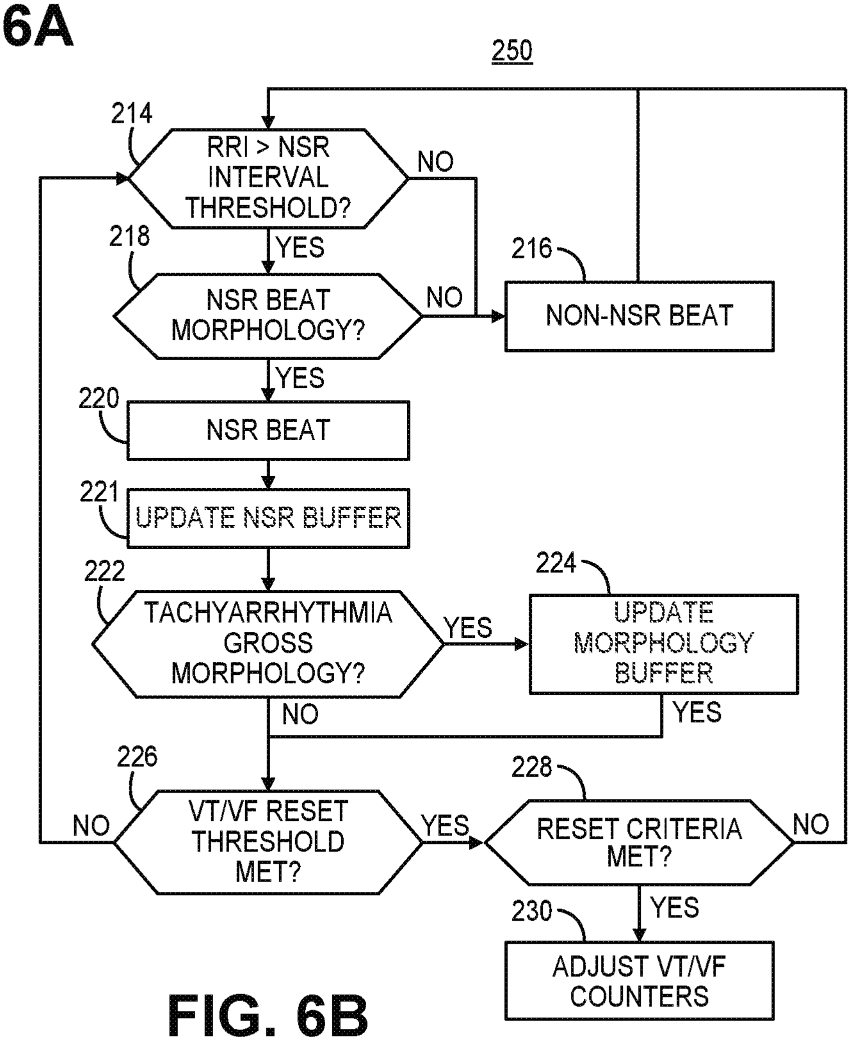
FIG. 6B is a flow chart of a method for controlling adjustments to ventricular tachyarrhythmia interval counters according to another example.

FIG. 6B is a flow chart 250 of a method for controlling adjustments of ventricular tachyarrhythmia interval counters according to another example. At block 214, the RRI ending with the currently sensed R-wave is compared to an NSR interval threshold. The NSR interval threshold may be established according to the example of FIG. 6A. In other examples, the NSR interval threshold may be set to a predetermined fixed interval, an interval based on the longest programmed tachyarrhythmia detection interval, an interval based on previously determined RRIs that are greater than the longest programmed tachyarrhythmia detection interval (e.g., an average RRI determined during a known sinus rhythm), or other methods. If the RRI is less than or equal to the NSR threshold, the current beat (corresponding to the currently sensed R-wave) is not detected as an NSR beat at block 216. The process may return to block 214 to sense the next R-wave and determine the next RRI. In other examples, tachyarrhythmia morphology classification may be determined at block 222 to update a morphology buffer as described below when NSR beat criteria are unmet at block 218.

When the current RRI is greater than the NSR threshold at block 214, control circuit 80 may analyze a segment of the second cardiac electrical signal corresponding to the currently sensed R-wave at block 218 to determine if an NSR beat morphology is detected to support the detection of an NSR beat. Example analysis of the second cardiac electrical signal and example criteria applied for detecting an NSR beat morphology at block 218 are described below in conjunction with FIGS. 7-9.

When the NSR beat morphology criteria are not satisfied at block 218, the current R-wave sensed event signal is not detected as an NSR beat at block 216. An NSR beat classification buffer may be updated on a first-in-first-out basis at block 216 based on the non-NSR beat detection. In response to detecting an NSR morphology at block 218, an NSR beat is detected at block 220. Control circuit 80 updates the NSR beat classification buffer and/or an NSR beat count accordingly at block 221. A buffer may be included in memory 82 for storing eight consecutive beat classifications as NSR beats or non-NSR beats on a first-in-first-out basis. Control circuit 80 may then determine an NSR beat count as the number of X NSR beats out of Y R-wave sensed events.

After updating the NSR beat classification buffer, or in simultaneous or parallel processing, control circuit 80 may determine if the current second cardiac electrical signal segment, corresponding to the currently sensed R-wave, meets tachyarrhythmia gross morphology criteria at block 222. If so, a tachyarrhythmia morphology classification buffer may be updated on a first-in-first out basis at block 224. The tachyarrhythmia morphology classification buffer stores, for example, the classification of 6 to 12 signal segments or 8 signal segments in one example as either a tachyarrhythmia morphology segment or non-tachyarrhythmia morphology segment. In some examples, when a second cardiac electrical signal segment is determined as an NSR beat, tachyarrhythmia morphology analysis is skipped at block 222. In other examples, the tachyarrhythmia morphology analysis for detecting a second cardiac electrical signal segment as having a tachyarrhythmia morphology may be performed before detecting an NSR beat and analysis for detecting an NSR beat may be skipped when the second cardiac electrical signal segment is detected as a tachyarrhythmia morphology signal segment. In still other examples, when tachyarrhythmia morphology criteria are satisfied, the segment may be classified as a tachyarrhythmia morphology segment regardless of whether the NSR beat criteria are met. The tachyarrhythmia morphology classification may supersede the NSR beat classification. In this case, the NSR buffer may not be updated to include an NSR beat classification in response to the NSR beat criteria being satisfied unless the tachyarrhythmia morphology criteria are unsatisfied for the same signal segment.

At block 226, control circuit 80 determines if the VT interval counter, VF interval counter and/or combined VT/VF interval counter has reached a reset threshold value as described above in conjunction with FIG. 5. For example, if a VF interval counter has reached a value of 7 or higher or the combined VT/VF interval counter has reached a value of 8 or higher, the reset threshold is met at block 226. If not met, control circuit 80 withholds any adjustment to the tachyarrhythmia interval counters and returns to block 214. In response to the reset threshold being reached, control circuit 80 determines whether NSR reset criteria and tachyarrhythmia morphology reset criteria are met at block 228. As generally described above in conjunction with FIG. 5, the NSR event count may be required to be greater than an NSR reset threshold value and the tachyarrhythmia morphology count may be required to be less than a withhold reset threshold value. Control circuit 80 may determine that an NSR reset threshold number of NSR intervals is detected when an NSR beat associated with each of the NSR intervals is detected based on an NSR morphology.

If the reset criteria are not met at block 228, no adjustment to the tachyarrhythmia interval counters is made and the process may return to block 214. When reset criteria are met, control circuit 80 adjusts the tachyarrhythmia interval counter(s) to predetermined value(s) or according to predetermined specifications. For example, as described above in conjunction with FIG. 5, the VF interval counter may be decreased from its current value to a value of 3. The VT interval counter, if enabled, may be reduced to a value of 2. A combined VT/VF interval counter may be adjusted to the combined count of the adjusted VT interval counter value and the adjusted VF interval counter value. Other predetermined or scaled adjustments to the tachyarrhythmia interval counter(s) may be performed as described above in conjunction with FIG. 5 in response to the reset criteria being met at block 228.

In some examples, the NSR interval threshold may be updated according to the method of FIG. 6A based on long cycle lengths regardless of the value of tachyarrhythmia interval counters, on an ongoing basis. Detection of NSR beats based on the NSR interval threshold and NSR beat morphology according to the methods of FIG. 6B, however, may be performed only after at least one tachyarrhythmia interval counter has a value greater than zero or other predetermined threshold value. For example, as generally described below in conjunction with FIG. 12, NSR beat detection may be enabled when the VF interval counter is at 3 or higher and/or the VT interval counter is at 2 or higher. In other examples, the buffering of long cycle lengths and determination of the NSR interval threshold may begin when a tachyarrhythmia interval counter is active, e.g., at a non-zero value or reached an R-sense confirmation threshold of 2, 3 or other predetermined value.

Figure 7:
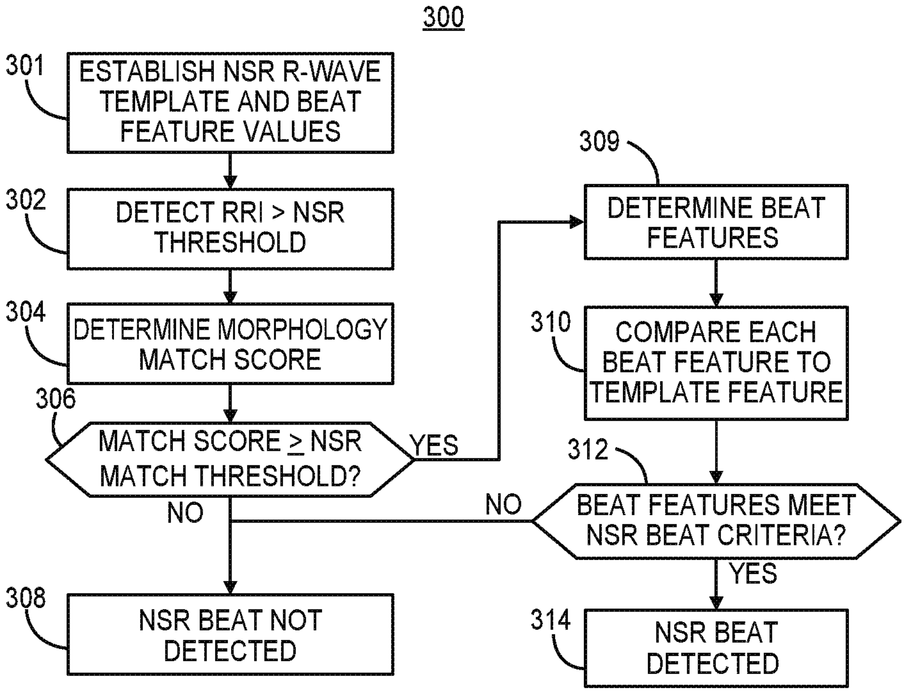
FIG. 7 is a flow chart of a method for detecting an NSR beat according to some examples.

FIG. 7 is a flow chart 300 of a method for detecting an NSR beat. At block 301, control circuit 80 establishes an NSR R-wave morphology template and NSR beat feature values. The NSR morphology template and NSR beat features represent the expected R-wave morphology during an NSR beat. The NSR template may be acquired during a slow, non-paced ventricular rhythm to represent a normal QRS waveform conducted from a depolarization arising from the sinus node in some examples. To establish the template and beat feature values at block 301, control circuit 80 may acquire a predetermined number of R-wave signals (or QRS complexes) from a cardiac electrical signal received from sensing circuit 86 during known NSR. For example, NSR may be confirmed manually by a user using external device 40 or automatically determined by control circuit 80 by detecting a normal heart rate (e.g., less than a tachyarrhythmia rate associated with VT/VF detection intervals) and/or regular, stable R-wave signals. For example, three or more R-wave signals may be acquired at block 301. These R-wave signals may be notch-filtered signals received from the second sensing channel 85, each corresponding to an R-wave sensed event signal received from the first sensing channel 83. The notch-filtered R-wave signal segments may be aligned in time relative to the time of the corresponding R-wave sensed event signal. In other examples, a different reference time point or sample number may be used to align the R-wave signal segments such as a maximum peak or other fiducial point. The notch-filtered R-wave signals may then be ensemble averaged to obtain an averaged R-wave signal to establish an NSR R-wave morphology template for use in detecting NSR beats. Wavelet transform coefficients may be determined from the averaged R-wave signal, e.g., using a Harr wavelet transform method. The digitized averaged R-wave signal and/or the wavelet transform coefficients may be stored in memory 82 as the NSR morphology template. In other examples, the NSR morphology template may be generated from the wavelet transform of a single R-wave signal acquired during NSR. The processing performed to generate an NSR morphology template and compare an unknown signal segment to an NSR morphology template as described below may include other techniques in the time domain or transformation techniques other than the wavelet transform method.

At block 301, control circuit 80 establishes reference NSR beat feature values, which may be determined from the averaged R-wave signal also used to generate the NSR morphology template. The reference NSR beat feature values determined at block 301 may include an R-wave polarity pattern, a peak time interval, and a normalized width metric. Example techniques for determining these specific NSR beat features are described in conjunction with FIGS. 8 and 9 below. The reference NSR beat feature values are stored in memory 82 for use in determining when NSR beat morphology criteria are satisfied.

In response to detecting an RRI that is greater than the NSR threshold interval at block 302, control circuit 80 determines a morphology match score at block 304. The morphology match score is determined between the established NSR R-wave morphology template and the second cardiac electrical signal segment buffered in response to the currently sensed R-wave (ending the RRI that is greater than the NSR threshold). The morphology match score may be determined by performing a wavelet transform on the second cardiac electrical signal segment to generate a set of wavelet coefficients for the unknown cardiac electrical signal waveform present in the second cardiac electrical signal segment. The wavelet coefficients may have predetermined weightings representative of the amplitudes of the frequency components of the signal waveform. These wavelet coefficients may be compared to the wavelet coefficients established for the NSR R-wave morphology template to determine the morphology match score. The morphology match score represents the correlation between the wavelet coefficients of the NSR R-wave morphology template and the wavelet coefficients of the waveform present in the second cardiac electrical signal segment, which may be aligned with the template based on a predetermined fiducial point such as the sample point at which the R-wave sensing threshold was crossed. A morphology match score may be determined using various template or morphology matching techniques for determining correlation between an NSR R-wave template or reference and the unknown cardiac electrical signal waveform. Such techniques may include various waveform correlation analyses, determination of multiple fiducial or characteristic points identified along the signal waveform and/or other determined waveform features such as positive and/or negative waveform area, amplitude, zero crossings, inflection points, peak slopes, etc. Determination of an NSR R-wave morphology is not limited to a specific matching technique for detecting a correlation between an unknown cardiac electrical signal segment and a known NSR R-wave template or reference.

At block 306, a template match score determined from a selected matching technique may be compared to an NSR match score threshold. The match score threshold may be set to 60, 70 or another predetermined value, below which the unknown cardiac signal waveform is not considered to be an NSR R-wave. In one example, when the morphology match score ranges from 1 to 100, the morphology match score threshold is set to 61. When the morphology match score is less than the threshold, the current beat is not detected as an NSR beat at block 308. When the morphology match score is equal to or greater than the NSR match threshold, control circuit 80 may determine each of the specific NSR beat features from the second cardiac electrical signal segment and compare them to the reference NSR beat features at blocks 309 and 310, respectively.

As described below in conjunction with FIGS. 8 and 9, the beat features determined at block 309 may include one or more of a polarity pattern of the cardiac electrical signal waveform peaks, a maximum peak time, a normalized width metric or other beat features. These features determined from the second cardiac electrical signal segment encompassing the time of an R-wave sensed from the first cardiac electrical signal may be compared to the reference values at block 310. When the beat features match the reference features according to predefined matching criteria, an NSR beat morphology is detected at block 314. When the beat features do not match the reference features, e.g., within a specified range, an NSR beat is not detected at block 308. This classification of the cardiac electrical signal segment, and corresponding currently sensed R-wave, as an NSR or non-NSR beat based on analysis of the corresponding second cardiac electrical signal segment at blocks 304 through 314, may be performed at block 104 of FIG. 5 or block 218 of FIG. 6B. Detection of an NSR beat may therefore include detecting an NSR morphology from the second cardiac electrical signal over a time segment that corresponds to an R-wave sensed from the first cardiac electrical signal at an RRI that is an NSR interval (e.g., greater than the NSR interval threshold) from a preceding cardiac event (sensed R-wave or ventricular pacing pulse). When an NSR beat is detected based on a detected NSR interval and a detected NSR morphology, which may include an overall waveform shape and specific beat features, the NSR beat classification buffer is updated at block 104 (FIG. 5) or block 221 (FIG. 6B) for use in controlling adjustments to the tachyarrhythmia interval counters when NSR beat classifications stored in the buffer meet reset criteria.

In some examples, the NSR beat detection criteria, which may include various thresholds, matching intervals, differences or ranges, applied to the morphology match score and/or specific morphology beat features for detecting an NSR beat may be adjustable. More stringent matching criteria may be applied by control circuit 80 when a relatively lower reset threshold number of NSR beats is required to decrease a tachyarrhythmia interval counter. The morphology matching criteria may be adjusted to relatively less stringent criteria when a relatively higher reset threshold number of NSR beats is required to decrease a tachyarrhythmia interval counter. For example, when the NSR reset threshold is set to 2 NSR beats identified out of 8 consecutively sensed R-waves, the morphology matching score may be required to be relatively higher, e.g., 71 or higher, and/or the specific beat features may be required to be within a relatively tight range of the respective reference values, e.g., within 15 to 20%. When the NSR reset threshold is set to a relatively higher number of NSR beats, e.g., 4 out of the most recent 10 sensed R-waves, the morphology matching score threshold may be lower, e.g., 61 or lower. Specific beat features may be required to be within a relatively wider range of the respective reference values, e.g., within 25 to 30%.

Figure 8:
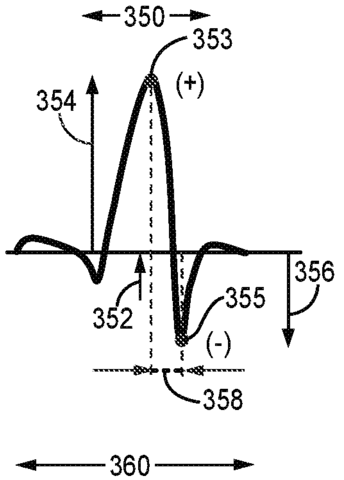
FIG. 8 is a diagram of one example of a notch-filtered cardiac electrical signal segment from which cardiac signal segment beat features are determined for detecting an NSR beat.

FIG. 8 is a diagram of one example of a notch-filtered cardiac electrical signal segment 350 from which cardiac signal segment beat features are determined at block 309 of FIG. 7 for detecting an NSR beat. Cardiac signal segment 350 may include a predetermined number of sample points before and after an R-wave sensed event signal 352 produced by sensing circuit 86. In one example, cardiac signal segment 350 used for determining beat features includes 48 sample points acquired at a sampling rate of 256 Hz, with the R-wave sensed event signal 352 aligned with the twenty-fourth sample point. In other examples, a higher or lower sampling rate may be used, e.g., a sampling rate of 512 Hz or 128 Hz. A correspondingly higher or lower number of sample points may be used to analyze the cardiac signal segment over the same or similar time interval extending before and after the time point that the R-wave was sensed.

The R-wave sensed event signal 352 may be produced when cardiac signal segment 350 crosses an R-wave sensing threshold but may be produced when a different cardiac electrical signal, e.g., from a different one of sensing channels 83 and 85, crosses the R-wave sensing threshold. For instance, the first sensing channel 83 may produce R-wave sensed event signal 352 in response to the first cardiac electrical signal received by first sensing channel 83 crossing an R-wave sensing threshold. The cardiac signal segment 350 may be buffered in memory 82 from the second cardiac electrical signal 78 received by control circuit 80 from the second sensing channel 85. The R-wave sensed event signal 352 from the first sensing channel 83 is used as a timing marker for selecting the beginning and ending sample points stored from the second cardiac electrical signal. In this way, the first sensing channel 83 may be used for sensing R-waves, and the second sensing channel 85 may be used for acquiring cardiac signal segments from a different sensing vector and/or sensing channel having different filtering or other signal processing properties. Each second cardiac electrical signal segment 350 corresponds to an R-wave sensed event signal 352 in that the segment 350 spans an interval of time that encompasses the R-wave sensed event signal 352.

A relatively short time segment 350 of the second cardiac electrical signal comprising and optionally centered on the time point of the R-wave sensing threshold crossing by the first cardiac electrical signal may be used to determine the specific beat features for detecting an NSR beat. The signal features determined as "beat features" from the relatively short time segment, e.g., 48 sample points (sampled at 256 Hz) or about 180 to 200 ms of the second cardiac electrical signal, characterize the sensed signal over a time interval corresponding to one isolated R-wave to verify that the signal features match NSR R-wave features. The time segment may correspond to at least the expected width of an NSR R-wave or an NSR QRS waveform. In still other examples, the time segment may correspond to at least the expected duration of a Q-T or R-T interval. In some examples, the relatively short time interval of the second cardiac electrical signal segment used for determining beat features for classifying NSR beats is a portion of a longer time interval 360 of the second cardiac electrical signal segment used for determining gross morphology metrics for classifying the second cardiac electrical signal segment as a tachyarrhythmia morphology as described below in conjunction with FIGS. 10 and 11.

One feature determined from cardiac signal segment 350 may be its peak polarity pattern. An R-wave signal may have a biphasic polarity having both a pronounced positive and pronounced negative peak. At other times, an R-wave signal may have a monophasic polarity pattern characterized by a single dominant peak, either positive or negative. Control circuit 80 may be configured to identify and discriminate between four polarity patterns that occur within the relatively narrow time segment of the second cardiac electrical signal: biphasic having a positive peak followed by a negative peak; biphasic having a negative peak followed by a positive peak; monophasic having a positive dominant peak, or monophasic having a negative dominant peak. Polarity pattern values may be assigned to each of the possible polarity patterns for buffering in memory 82 for a predetermined number of cardiac signal segments. For instance, the four polarity patterns listed above may be assigned respective values of 1 through 4. In other examples, polarity patterns identified by control circuit 80 may not be limited to the four patterns listed above; control circuit 80 may be configured to identify fewer, additional or different polarity patterns than the four listed here. Polarity patterns that are identified may be tailored to an individual patient or based on implant locations of sensing electrode vectors. The polarity pattern characterizes the R-wave polarity pattern during NSR within the short time segment, e.g., approximately 180 to 200 ms, that encompasses the R-wave sensed event signal. For example, an R-wave signal may include more than two pronounced peaks in a tri-phasic signal or a signal may have a polarity pattern including a pronounced split positive peak and/or a pronounced split negative peak.

Control circuit 80 may determine the polarity pattern of cardiac signal segment 350 by determining the maximum positive amplitude 354 (of the maximum peak 353) and the maximum negative amplitude 356 (of the minimum peak 355). The greatest absolute value of the maximum positive and negative amplitudes 354 and 356, respectively, is identified and may be used by control circuit 80 to set a polarity pattern amplitude threshold. If the absolute values of both of the maximum positive amplitude 354 and minimum negative amplitude 356 are greater than the polarity pattern amplitude threshold, the cardiac signal segment 350 is determined to have a biphasic polarity pattern. If only one of the maximum amplitudes 354 or 356 is greater than the polarity pattern amplitude threshold, the cardiac signal segment is determined to have a monophasic polarity pattern.

In an illustrative example, the polarity pattern amplitude threshold is set to be 25% of the largest one of the maximum positive amplitude 354 and the absolute minimum negative amplitude 356. In the particular example shown in FIG. 8, maximum positive amplitude 354 is greater in absolute value than minimum negative amplitude 356. Control circuit 80 therefore uses the maximum positive amplitude 354 to set the polarity pattern amplitude threshold as 25% of maximum positive amplitude 354. The absolute value of the minimum negative amplitude 356 is compared to the polarity pattern amplitude threshold. Since it is greater than the polarity pattern amplitude threshold, i.e., greater than 25% of the maximum positive amplitude 354 in this example, the cardiac signal segment 350 is determined to have a biphasic polarity pattern.

The control circuit 80 may further determine that the positive peak 353 occurs earlier in time than the negative peak 355 yielding a polarity pattern of biphasic, positive peak first. The sample point numbers of maximum peak 353 and minimum peak 355 may be compared to determine if the biphasic pattern is positive peak first or negative peak first. The sample points in cardiac signal segment 350 may be numbered consecutively from beginning to end, e.g., from 1 to 48 when 48 sample points are included in cardiac signal segment 350. A lower sample point number of maximum peak 353 and a higher sample point number of minimum peak 355 indicate a positive peak first polarity pattern. Control circuit 80 may store a value in memory 82 indicating that the polarity pattern of cardiac signal segment 160 is biphasic, positive peak first.

A second beat feature determined from the relatively short cardiac signal segment 350 may be the peak time interval 358. In the example of a biphasic polarity pattern, the peak time interval 358 may be determined as the time interval between the maximum peak 353 and the minimum peak 355. This peak time interval 358 may be determined and stored in memory 82 for cardiac signal segment 350 as the difference between the respective sample point numbers of the maximum positive peak 353 and the minimum negative peak 355. The peak time interval 358 may be determined from a selected, specified reference time point during the signal segment 350 to the maximum peak, where the reference time point may be different depending on the peak polarity pattern as described below.

Figure 9:
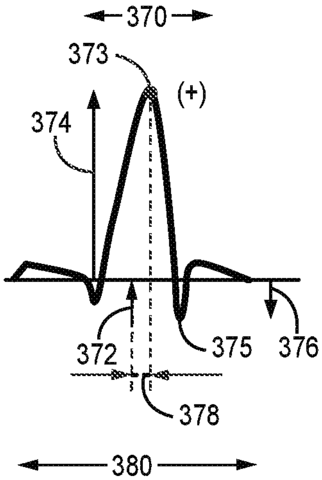
FIG. 9 is a diagram of another example of a notch-filtered cardiac electrical signal segment from which cardiac signal segment beat features are determined for detecting an NSR beat.

FIG. 9 is a diagram of an example notch-filtered cardiac signal segment 370 having a monophasic polarity pattern. Signal segment 370 may be acquired as described in conjunction with FIG. 8 above, as a predetermined number of signal sample points, e.g., 48 sample points sampled at 256 Hz, centered on an R-wave sensed event signal 372. Relatively short signal segment 370 may be a portion of a relatively longer segment 380 buffered from the second cardiac electrical signal for determining gross morphology metrics used in detecting a tachyarrhythmia morphology of the segment, e.g., as described below in conjunction with FIGS. 10 and 11. The amplitude 374 of maximum positive peak 373 is used by control circuit 80 to set the polarity pattern amplitude threshold because it is greater (in absolute value) than the amplitude 376 of minimum negative peak 375. In this example, the absolute value of the minimum negative amplitude 376 is less than the polarity pattern amplitude threshold, which may be set to one-fourth of the maximum positive amplitude 374. The maximum positive peak 373 is therefore the only dominant peak. Control circuit 80 identifies cardiac signal segment 370 as having a monophasic, positive peak polarity pattern and stores a polarity pattern value in memory 82 indicating this polarity pattern for cardiac signal segment 370.

When the peak polarity pattern is determined to be monophasic, the control circuit 80 may determine the peak time interval 378 using a different method than the method used to determine the peak time interval 358 of a biphasic polarity pattern signal 350 as shown in FIG. 8. The peak time interval 378 of a monophasic signal 370 may be determined as the time interval, or sample point number difference, between the R-wave sensed event signal 372 and the dominant peak, which is maximum positive peak 373 in this example.

A third beat feature that may be determined (e.g., at block 309 of FIG. 7) from relatively short cardiac signal segments 350 and 370 (of FIGS. 8 and 9), in addition to the peak time interval and the peak polarity pattern, may be a normalized width metric. The normalized width metric is determined as an indication of the narrowness of the sensed R-wave. When the signal waveform in the second cardiac electrical signal corresponding to an R-wave sensed from the first cardiac electrical signal, is relatively narrow, it is likely a true R-wave. When the signal waveform is relatively wide, the signal may be an oversensed signal, e.g., a P-wave, T-wave, or non-cardiac noise, or even a fibrillation wave. To obtain a width metric that is correlated to the width of the waveform corresponding in time to an R-wave sensed event signal, the cardiac signal segment 350 or 370 may be rectified and all sample point amplitudes may be summed to obtain an "area" defined by the rectified signal segment 350 or 370. The area of the signal 350 or 370 may be divided by the largest absolute value of either the maximum peak amplitude 354 or 374 or minimum peak amplitude 356 or 376 of the respective signal segment (which may be thought of as the "height" of the signal) to obtain the normalized width metric. The normalized width metric will be relatively low when the sample points within the short second cardiac electrical signal segment include relatively low amplitude signal points, e.g., surrounding a true R-wave peak, indicating a steep and relatively narrow signal waveform as evidence of a true NSR R-wave. When the signal waveform is relatively wide, the sample points spanning the short second cardiac electrical signal segment will include generally higher amplitudes relative to the maximum peak, resulting in a higher normalized width metric, which is evidence against a NSR R-wave.

Each of the three beat features, namely peak polarity pattern, peak time interval and normalized width metric, may be determined and stored for each buffered second cardiac electrical signal segment analyzed for detecting an NSR beat. The reference values of the peak polarity pattern, peak time interval, and normalized width metric may be previously established at block 301 of FIG. 7, from the NSR R-wave template, e.g., from the ensemble average of multiple, time-aligned NSR R-waves. The beat feature reference values may be established using the beat feature determination techniques described in conjunction with FIGS. 8 and 9. In this way, cardiac signal segment beat features determined from signal segments acquired during an unknown heart rhythm may be compared to analogous reference values of NSR R-wave template beat features for detecting an NSR beat and updating an NSR beat classification buffer.

When the respective beat features are within a threshold range of the reference feature, or match the reference value in the case of polarity pattern, the signal segment may be classified as an NSR beat and the classification stored in the NSR beat classification buffer. As an illustrative example, when the peak distance is within 7 sample points of the reference peak distance the peak distance is determined to match the NSR reference feature. When the normalized width metric is within 30 ADC units of the reference width metric, the normalized width metric is determined to match the NSR reference feature. When these two beat features match the respective NSR reference features, the polarity pattern matches the NSR polarity pattern, and the overall morphology matching score is greater than matching score threshold (e.g., 60), the segment may be classified as a NSR beat in the NSR buffer. Otherwise, the segment may be classified as a non-NSR beat in the NSR buffer.

Figure 10:
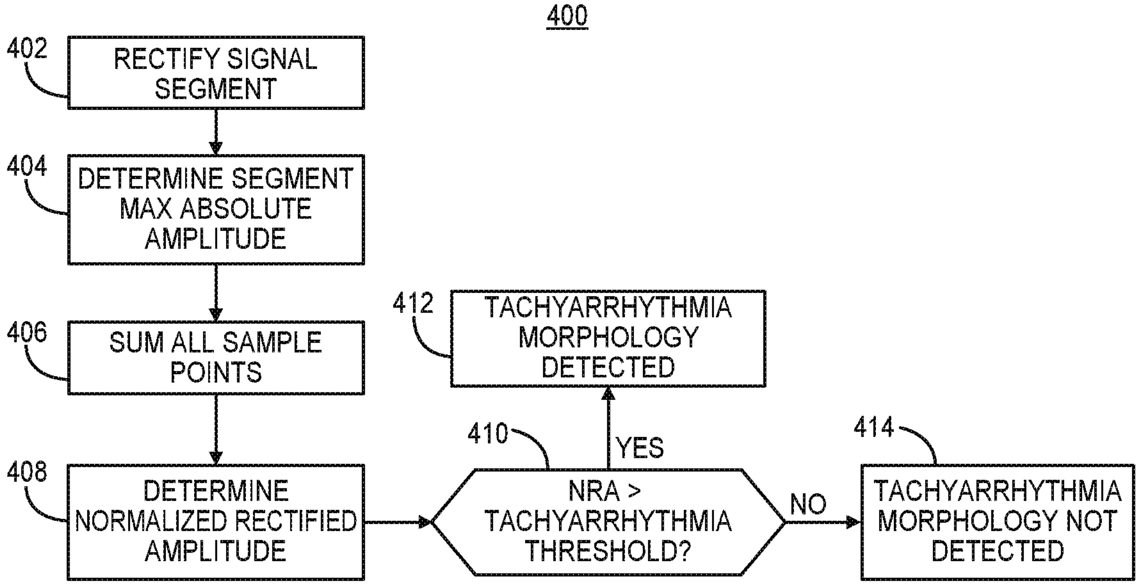
FIG. 10 is a flow chart of a method for determining a gross morphology metric for detecting a tachyarrhythmia morphology of a cardiac signal segment according to one example.

FIG. 10 is a flow chart 400 of a method for determining a gross morphology metric for detecting a tachyarrhythmia morphology according to one example. The method of flow chart 400 may be performed at block 106 of FIG. 5 or block 218 of FIG. 6B to analyze a second cardiac electrical signal segment for detecting evidence of a tachyarrhythmia morphology. In the example of FIG. 10, a gross morphology amplitude metric is determined to detect a tachyarrhythmia morphology of the second cardiac electrical signal segment. The time interval over which the second cardiac electrical signal segment is buffered for use in determining gross morphology metrics may be longer than the time interval used to determine beat features as described above. For example, the gross morphology metrics may be determined using all sample points spanning a time interval that is about twice as long as the time interval used for determining the beat features. For instance, a 360 ms segment of the second cardiac electrical signal may include 92 sample points when the sampling rate is 256 Hz, with 24 of the sample points occurring after the R-wave sensed event signal that triggered the storage of the signal segment and 68 sample points extending from the R-wave sensed event signal earlier in time from the R-wave sensed event signal. In this way, the second cardiac electrical signal segment used to detect beat features as described above may start later (closer to the sensed R-wave) and end with the same sample point (after the sensed R-wave) as the second cardiac electrical signal segment used to detect a tachyarrhythmia morphology.

At block 402, the second cardiac electrical signal segment stored on a triggered basis in response to an R-wave sensed event signal may be rectified. In some examples, a 360 ms segment of the notch-filtered second cardiac electrical signal may be rectified by rectifier 75 included in the second sensing channel 85. At block 402, the buffered, rectified signal segment may be retrieved by control circuit 80 from memory 82. In other examples, a notch-filtered segment of the second cardiac electrical signal may be buffered in memory 82, and control circuit 80 may perform the rectification of the stored signal segment at block 402. Control circuit 80 may determine the maximum absolute amplitude of the rectified, notch-filtered signal segment at block 404. The maximum absolute amplitude may be determined from among all sample points spanning the relatively longer second cardiac electrical signal segment.

At block 406, the amplitudes of all sample points of the rectified signal segment are summed. At block 408, the gross morphology metric of the signal segment is determined as a normalized rectified amplitude (NRA) based on the maximum absolute amplitude determined at block 404 and the summed sample point amplitudes determined at block 406. In one example, the NRA is determined as a predetermined weighting or multiple of the summation of all sample point amplitudes of the notch-filtered and rectified signal segment normalized by the maximum amplitude. For instance, the NRA may be determined as four times the summed amplitudes divided by the maximum absolute amplitude, which may be truncated to an integer value. This NRA may be determined as a gross morphology amplitude metric at block 105 of FIG. 5 or block 222 of FIG. 6B for detecting a tachyarrhythmia morphology.

This gross morphology amplitude metric may be inversely correlated to the probability of the signal segment sample points being at a baseline amplitude during the time interval of the signal segment. The higher the gross morphology amplitude metric is, the lower the probability that the signal is at a baseline amplitude at any given time point during the relatively longer time interval of the signal segment comprising the sensed R-wave signal. A relatively low probability that the signal is at baseline during the time interval may be correlated to a tachyarrhythmia morphology, e.g., a ventricular fibrillation morphology, which may resemble a sinusoidal waveform, having a low number of sample points at any given time at the baseline compared to baseline signal segments that occur between NSR R-waves. When the gross morphology amplitude metric exceeds a tachyarrhythmia morphology threshold value, the more likely the second cardiac electrical signal segment possesses a tachyarrhythmia morphology. When the gross morphology amplitude metric is less than the threshold value, the higher the probability that the signal is at a baseline amplitude at a given time point during the relatively longer time interval of the signal segment, extending earlier from the sensed R-wave. A relatively higher probability of a signal sample point being at baseline during the time interval of the relatively longer signal segment may be correlated to a true, relatively narrow NSR R-wave signal occurring during the signal segment, with baseline amplitude portions of the signal segment occurring before and after the true R-wave.

At block 410, the NRA is compared to a tachyarrhythmia threshold. The tachyarrhythmia threshold for detecting a tachyarrhythmia gross morphology may be between 100 and 150 and is 125 in some examples, such as when 92 sample points are summed and multiplied by a factor of four and normalized by the maximum absolute amplitude. The threshold applied at block 410 to discriminate between a tachyarrhythmia morphology and a non-tachyarrhythmia morphology in the second cardiac electrical signal segment will depend on various factors such as the sampling rate, amplification and number of sample points summed, the multiplication or weighting factor of the summed sample points, etc.

When the NRA is greater than the tachyarrhythmia threshold at block 410, evidence of a tachyarrhythmia morphology is detected, which may preclude adjusting a tachyarrhythmia interval counter to a lower value. When a threshold number of second cardiac signal segments are counted as having a tachyarrhythmia morphology, e.g., based on a relatively high gross morphology amplitude metric, control circuit 80 may detect a tachyarrhythmia morphology and update a tachyarrhythmia morphology classification buffer at block 106 of FIG. 5 (or blocks 222 and 224 of FIG. 6B) used for counting tachyarrhythmia morphology segments. When the NRA is less than the tachyarrhythmia threshold at block 410, a tachyarrhythmia morphology is not detected at block 414, at least based on the gross morphology amplitude metric but may be detected based on other gross morphology metrics.

Figure 11:
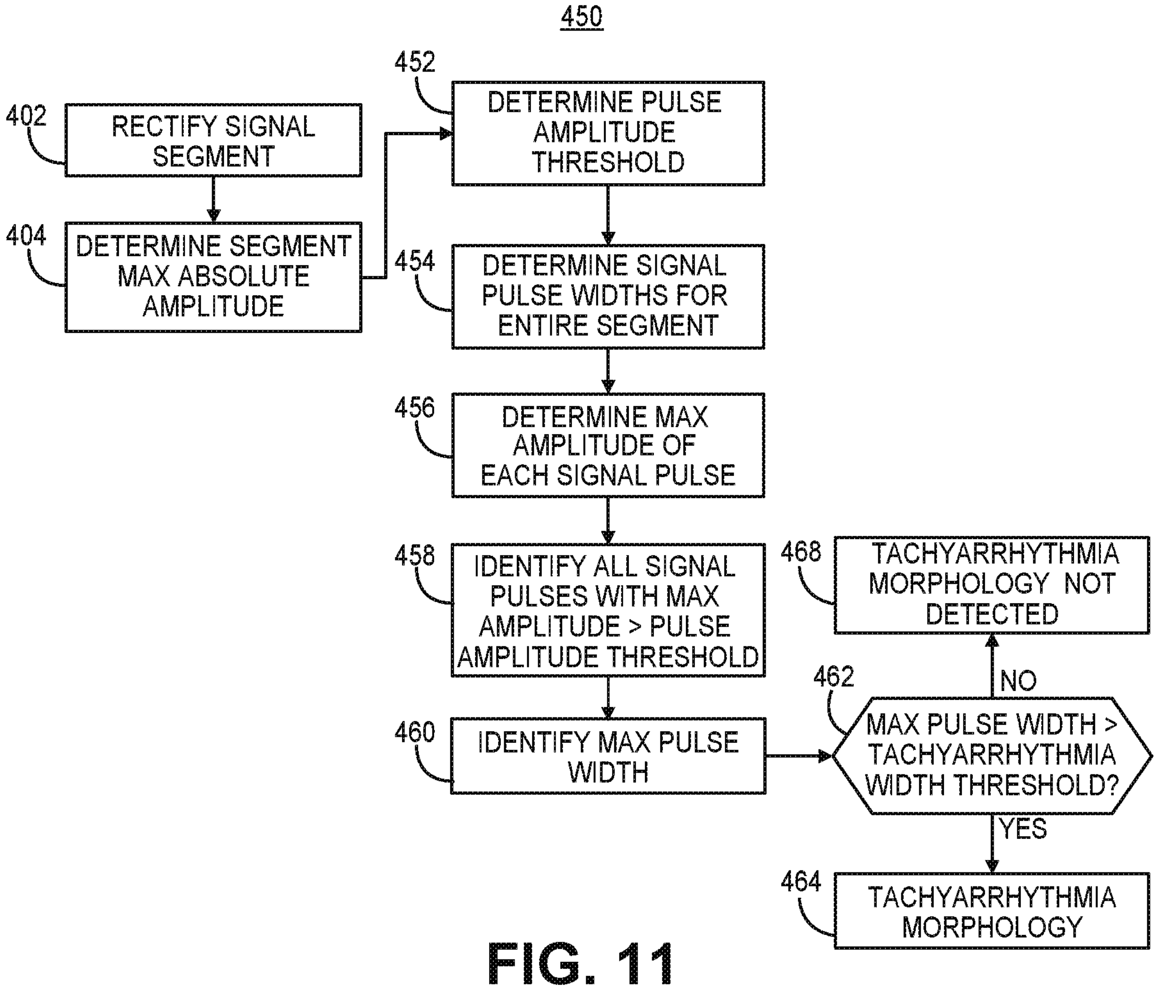
FIG. 11 is a flow chart of a method for detecting a tachyarrhythmia morphology of a cardiac electrical signal segment according to another example.

FIG. 11 is a flow chart 450 of a method for detecting a tachyarrhythmia morphology of a second cardiac electrical signal segment according to another example. In this example, the tachyarrhythmia morphology detection is based on a gross morphology signal width metric. The process of flow chart 450 may be performed by ICD 14 for determining a gross morphology signal width metric at block 106 of FIG. 5 or block 222 of FIG. 6B, for instance. Blocks 402 and 404 correspond to identically-numbered blocks described above in conjunction with FIG. 10. The notch-filtered, rectified signal segment obtained from the second sensing channel 85 at block 402, comprising a time point of an R-wave sensed event signal generated by the first sensing channel 83, is analyzed to detect a gross morphology that is indicative of a tachyarrhythmia. At block 404, control circuit 80 determines a maximum absolute amplitude of the rectified signal segment.

Control circuit 80 determines a pulse amplitude threshold at block 452 based on the maximum absolute amplitude determined at block 404. This pulse amplitude threshold may be used for identifying a signal pulse during the second cardiac electrical signal segment having a maximum signal width out of all signal pulses occurring during the time interval of the second cardiac electrical signal segment. For example, the pulse amplitude threshold used for determining the gross morphology signal width metric may be set to half the maximum absolute amplitude of the rectified, notch-filtered signal segment.

At block 454, control circuit 80 determines the signal width for all signal pulses of the second cardiac electrical signal segment corresponding to the currently sensed R-wave. A signal pulse may be identified by identifying two consecutive zero amplitude or baseline amplitude sample points of the rectified signal segment (or two consecutive zero crossings of a non-rectified signal segment). All signal pulses between two consecutive baseline amplitude sample points are identified at block 454. The signal width of each identified signal pulse is determined as the number of sample points (or corresponding time interval) between the pair of consecutive baseline amplitude sample points.

The maximum amplitude of each signal pulse is determined at block 456. All signal pulses having a maximum amplitude that is greater than the pulse amplitude threshold determined at block 452 are identified at block 458. For example, all signal pulses having a maximum amplitude that is at least half the maximum absolute amplitude determined at block 404 are identified. The maximum signal pulse width is determined at block 460 by comparing the signal pulse widths of all signal pulses having a maximum amplitude that is at least the pulse amplitude threshold. The maximum signal pulse width out of all of the identified signal pulses meeting the amplitude threshold requirement may be determined as the gross morphology signal width metric at block 460.

Control circuit 80 compares the maximum signal pulse width to a tachyarrhythmia width threshold at block 462. In one example, the tachyarrhythmia width threshold is set between 15 and 25 sample points, e.g., to 20 sample points when the sampling rate is 256 Hz. When the maximum signal pulse width is less than or equal to the width threshold, control circuit 80 does not detect a tachyarrhythmia morphology at block 468 based on the signal width metric. A tachyarrhythmia morphology may be detected based on another gross morphology metric, however, such as the gross morphology amplitude metric described in conjunction with FIG. 10.

The gross morphology signal width metric is correlated to the probability of the signal segment having a tachyarrhythmia morphology. For example, a relatively high gross morphology signal width metric may be evidence of a tachyarrhythmia morphology, such as relatively wide ventricular fibrillation waves in contrast to a narrow NSR R-wave. Conversely, a relatively low gross morphology signal width metric may be evidence of a relatively narrow, NSR R-wave occurring during the time interval of the second cardiac electrical signal segment.

When the maximum pulse width is greater than the tachyarrhythmia morphology threshold at block 462, tachyarrhythmia morphology is detected at block 464. The relatively wide signal pulse is evidence of a tachyarrhythmia morphology present in the segment of the second cardiac electrical signal being analyzed. Evidence of the tachyarrhythmia morphology may preclude resetting or adjusting a tachyarrhythmia interval counter, e.g., at block 114 of FIG. 5 or block 240 of FIG. 6B, even when NSR beats have been detected. When less than a threshold number of the cardiac electrical signal segments analyzed are determined to have a tachyarrhythmia morphology, NSR beat detections support a resetting or adjustment of the tachyarrhythmia interval counters to avoid a VT or VF detection due to variability in the R-wave amplitude and/or incidence of noise over the required NID.

The gross morphology amplitude metric determined by the method of FIG. 10 and the gross morphology signal width metric determined by the method of FIG. 11 may both be determined by control circuit 80 and used in combination to detect a tachyarrhythmia morphology at block 106 of FIG. 5 or block 222 of FIG. 6B. Evidence of a tachyarrhythmia morphology based on the gross morphology metrics prevents resetting or adjustment of a tachyarrhythmia interval counter, regardless of NSR beat detections in some examples. A second cardiac electrical signal segment that has a relatively high gross morphology amplitude metric and/or relatively high gross morphology signal width metric is evidence of a tachyarrhythmia morphology. In various examples, both the gross morphology amplitude metric and the gross morphology signal width metric may be determined and compared to respective tachyarrhythmia morphology thresholds. In some examples, only one of the gross morphology amplitude metric or the gross morphology signal width metric may be required to be greater than the respective tachyarrhythmia morphology threshold for the signal segment to be identified and counted as a tachyarrhythmia gross morphology signal segment. When tachyarrhythmia morphology criteria are met, e.g., at least one or both of the gross morphology amplitude metric and the gross morphology signal width metric are less than a respective tachyarrhythmia morphology threshold, a threshold number of identified NSR beats may be used for resetting or adjusting the tachyarrhythmia interval counter(s).

Figure 12:
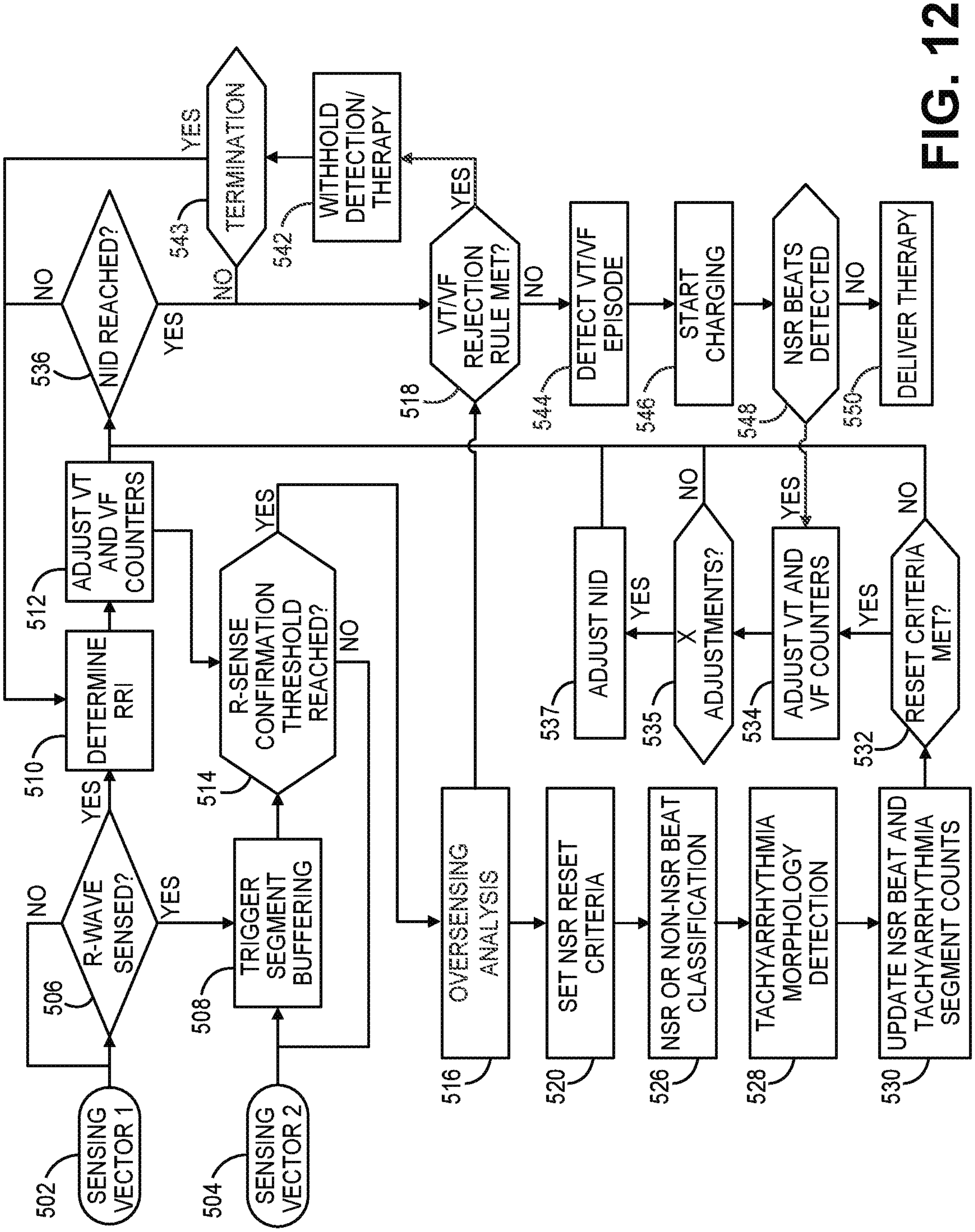
FIG. 12 is a flow chart of a method performed by an ICD for detecting ventricular tachyarrhythmia according to some examples.

FIG. 12 is a flow chart 500 of a method performed by ICD 14 for detecting ventricular tachyarrhythmia according to some examples. At blocks 502 and 504, two different sensing electrode vectors may be selected by sensing circuit 86 for receiving a first cardiac electrical signal by a first sensing channel 83 and a second cardiac electrical signal by a second sensing channel 85, respectively (see FIG. 4). The two sensing electrode vectors may be selected by switching circuitry included in sensing circuit 86 under the control of control circuit 80. In some examples, the two sensing electrode vectors are programmed by a user and retrieved from memory 82 by control circuit 80 and passed to sensing circuit 86 as vector selection control signals.

The first sensing vector selected at block 502 for sensing a first cardiac electrical signal may be a relatively short bipole, e.g., between electrodes 28 and 30 or between electrodes 28 and 24 of lead 16 or other electrode combinations as described above. The relatively short bipole may include electrodes that are in relative close proximity to each other and to the ventricular heart chambers compared to the second sensing vector selected at block 504, to provide sensing of a relatively "near-field" ventricular signal for sensing R-waves. The first sensing vector may be a vertical sensing vector (with respect to an upright or standing position of the patient) or approximately aligned with the cardiac axis for maximizing the amplitude of R-waves in the first cardiac electrical signal for reliable R-wave sensing. The first sensing vector, however, is not limited to any particular interelectrode spacing or orientation and may be selected as any available electrode pair.

The second sensing electrode vector used to obtain a second cardiac electrical signal at block 504 may be a relatively long bipole having an inter-electrode distance that is greater than the first sensing electrode vector. For example, the second sensing electrode vector may be selected as the vector between one of the pace sense electrodes 28 or 30 and ICD housing 15, one of defibrillation electrodes 24 or 26 and housing 15 or other combinations of one electrode along the distal portion of the lead 16 and the housing 15. This second sensing vector may be orthogonal or almost orthogonal to the first sensing vector in some examples, but the first and second sensing vectors are not required to be orthogonal vectors. The second sensing electrode vector may receive a relatively more global or far-field cardiac electrical signal compared to the first sensing electrode vector. The second cardiac electrical signal received by the second sensing vector selected at block 504 may be analyzed by control circuit 80 for detecting NSR beat morphology and tachyarrhythmia gross morphology. In other examples, the sensing vector 1 and sensing vector 2 may be the same sensing vector. In some examples, sensing vector 1 and sensing vector 2 are the same sensing vector but received by two different sensing channels of sensing circuit 86 having different filtering and/or other signal processing features to sense two different cardiac electrical signals, one for detecting R-waves and one for performing morphological analysis for detecting NSR beats and tachyarrhythmia morphology. In other examples, a single sensing channel may be provided for sensing a cardiac electrical signal used for sensing R-waves and performing morphology analysis for detecting NSR beats and tachyarrhythmia morphology.

Sensing circuit 86 may produce an R-wave sensed event signal at block 506 in response to the first sensing channel 83 detecting an R-wave sensing threshold crossing by the first cardiac electrical signal. The R-wave sensed event signal may be passed to control circuit 80. In response to the R-wave sensed event signal, down-going "yes" branch of block 506, control circuit 80 is triggered at block 508 to store a segment of the second cardiac electrical signal received from the second sensing channel 85 (via the second sensing vector selected at block 504) over a predetermined time interval. Segments of the second cardiac electrical signal may be stored in a circulating buffer of memory 82 configured to store multiple sequential segments, where storage of each segment is triggered by an R-wave sensed event signal produced by the first sensing channel 83. A digitized segment of the second cardiac electrical signal may be 100 to 500 ms long, for example, including sample points before and after the time of the R-wave sensed event signal. The segment of the second cardiac electrical signal may or may not be centered in time on the R-wave sensed event signal received from sensing circuit 86. For instance, the segment may extend 100 ms after the R-wave sensed event signal and be 200 to 500 ms in duration such that the segment extends from about 100 to 400 ms before the R-wave sensed event signal to 100 ms after. In other examples, the segment may be centered on the R-wave sensed event signal or extend a greater number of sample points after the R-wave sensed event signal than before. In one example, the buffered segment of the second cardiac electrical signal is at least 50 sample points obtained at a sampling rate of 256 Hz, or about 200 ms. In another example, the buffered segment is at least 92 sample points, or approximately 360 ms, sampled at 256 Hz and is available for analysis for detecting NSR beats as well as other analysis for confirming R-wave sensing, such as analysis for noisy signal segments or oversensing.

Memory 82 may be configured to store a predetermined number of second cardiac electrical segments, e.g., at least 1 and in some cases two or more cardiac electrical signal segments, in circulating buffers of memory 82 such that the oldest segment is overwritten by the newest segment triggered by a currently sensed R-wave. In some examples, each segment is analyzed for detecting an NSR beat morphology and updating the NSR beat classification buffer. In other examples, previously stored segments may never be analyzed for NSR beat detection and may be overwritten if an R-sense confirmation threshold number of tachyarrhythmia intervals is not reached at block 514 as described below. In some examples, at least one segment of the second cardiac electrical signal may be stored and if not needed for detecting NSR beats for use in adjusting tachyarrhythmia interval counters, the segment may be overwritten by the next segment corresponding to the next R-wave sensed event signal.

In addition to buffering a segment of the second cardiac electrical signal, control circuit 80 responds to the R-wave sensed event signal produced at block 506 by determining an RRI at block 510 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters at block 512. If the RRI is longer than a tachycardia detection interval (TDI), the tachyarrhythmia interval counters remain unchanged. If the RRI is shorter than the TDI but longer than a fibrillation detection interval (FDI), e.g., if the RRI is in a tachycardia detection interval zone, a VT interval counter is increased at block 512. If the RRI is shorter than or equal to the FDI, a VF interval counter is increased at block 512. In some examples, a combined VT/VF interval counter is increased if the RRI is less than the TDI.

After updating the tachyarrhythmia interval counters at block 512, tachyarrhythmia detector 92 compares the counter values to an R-sense confirmation threshold at block 514 and to VT and VF detection thresholds at block 536. If a VT or VF detection interval counter has reached an R-sense confirmation threshold, "yes" branch of block 514, the second cardiac electrical signal buffered from sensing channel 85 may be analyzed to detect NSR beats for use in adjusting the VT and VF interval counters as needed. The second cardiac electrical signal may also be analyzed for detecting various types of oversensing, which may be causing false R-wave sensed event signals to be produced by the first sensing channel 83, resulting in VT and/or VF counters being increased at block 512. The R-sense confirmation threshold may be a VT or VF interval count that is greater than a count of one or another higher threshold value.

Different R-sense confirmation thresholds may be applied to the VT interval counter and the VF interval counter. For example, the R-sense confirmation threshold may be a count of two on the VT interval counter and a count of three on the VF interval counter. In other examples, the R-sense confirmation threshold is a higher number, for example five or higher, but may be less than the number of intervals required to detect VT or VF. In addition or alternatively to applying an R-sense confirmation threshold to the individual VT and VF counters, an R-sense confirmation threshold may be applied to a combined VT/VF interval counter. It is recognized that in some examples, VT detection may not be enabled and VF detection may be enabled in ICD 14. In this case, only a VF interval counter is updated at block 512 in response to RRI determinations, and the R-sense confirmation threshold may be applied to the VF interval counter at block 514.

If the R-sense confirmation threshold is not reached by any of the tachyarrhythmia interval counters at block 514, the control circuit 80 waits for the next R-wave sensed event signal at block 508 to buffer the next segment of the second cardiac electrical signal. If the R-sense confirmation threshold is reached at block 514, e.g., when the VF interval counter is at a value of at least 2 or the VT interval counter is at a value of at least 3, the control circuit 80 begins analysis of the second cardiac electrical signal segments for detecting NSR beats. Other analyses of the second cardiac electrical signal segments for confirming a sensed R-wave, detecting various types of oversensing and/or detecting evidence of a supraventricular tachyarrhythmia (SVT) may also be performed in various examples.

At block 516, control circuit 80 may retrieve one or more notch filtered signal segments stored in the circulating buffer in memory 82 for performing various signal analyses that may confirm or reject tachyarrhythmia interval detection. In some examples, the stored second cardiac electrical signal segments are notch filtered by control circuit 80, e.g., by a firmware implemented notch filter, after the R-sense confirmation threshold is reached. In other examples, the notch-filtered signal received from the second sensing channel 85 as shown in FIG. 4 is buffered in memory 82 for retrieval by control circuit 80. As described above, for some analyses performed on the second cardiac electrical signal for detecting NSR beats and tachyarrhythmia morphology, a notch-filtered, rectified segment of the second cardiac electrical signal may be used. In other analyses, a non-rectified, notch filtered second cardiac electrical signal segment is used by control circuit 80.

At block 516, control circuit 80 may perform various analyses for detecting oversensing signal segments. An oversensing signal segment may be detected based on an analysis of the second cardiac electrical signal segments performed to detect noise that may be oversensed as false R-waves from the first cardiac electrical signal. A noisy signal segment that may be identified as an oversensing signal segment at block 516 may include noise signals due to non-cardiac muscle noise (myopotentials), electromagnetic interference, or other electrical noise. An oversensing signal segment may additionally or alternatively be identified at block 516 based on an analysis of the second cardiac electrical signal segment for detecting likely cardiac event oversensing, such as T-wave oversensing or P-wave oversensing leading to false R-wave sensed event signals produced by the first sensing channel. Multiple analyses for detecting different types of possible oversensing leading to the R-wave sensed event signal that triggered the storage of the second cardiac electrical signal segment may be performed at block 516. In some examples, the results of the oversensing analysis performed at block 516 may be used in setting a VT/VF detection rejection rule at block 518 as described below. Various examples of analyses of second cardiac electrical signal segments that may be performed at block 516 for identifying actual or potential noise-related or cardiac event oversensing are described in U.S. Pat. No. 10,406,373 (Zhang, et al.) and U.S. Pat. No. 9,956,423 (Zhang, et al.), both of which are incorporated herein by reference in their entirety.

At block 520, control circuit 80 may set the NSR reset criteria applied to detected NSR beats determining when to adjust a tachyarrhythmia interval counter. In some examples, control circuit 80 may set NSR reset criteria at block 520 based on the oversensing analysis performed at block 516. The NSR reset criteria may be set based on a history of noisy signal segment detections, a history of oversensing detections, and/or the programmed NID required to detect VT or VF. For example, if one or more second cardiac electrical signal segments have been identified as noisy signal segments, SVT signal segments, or oversensing of a T-wave or P-wave, the threshold number of NSR beats required for causing resetting or adjustment of the tachyarrhythmia interval counter(s) may be reduced. Noisy signal segments, SVT signal segments, T-wave oversensing or P-wave oversensing may be detected based on an analysis of the second cardiac electrical signal segments, which may include determining various features of the signal segments and/or a morphological analysis of the second cardiac electrical signal segments. These analyses may correspond to any of the analyses disclosed in the above-incorporated references. Any technique for detecting oversensing or noise in a cardiac electrical signal segment may be applied at block 516. When no noise or oversensing detections have been made, the number of NSR beats required to reset a tachyarrhythmia interval counter may be set to a relatively higher threshold, e.g., at least three NSR beat detections out of eight cardiac electrical signal segments analyzed. When a signal segment is identified as an oversensing segment due to potential or actual oversensing of cardiac events or non-cardiac noise being detected, the chance that short RRIs are being detected and counted as tachyarrhythmia intervals in the presence of an underlying NSR is increased. As such, when one or more segments are detected as noisy and/or one or more segments are identified as oversensed T-waves or P-waves, the NSR reset threshold for adjusting a tachyarrhythmia interval counter may be decreased, e.g., to two or even one detected NSR beat.

Additionally or alternatively, the NSR reset criteria set a block 520 may be based on the currently programmed NID for detecting VT or VF. For example, when the VF NID is set to 30 VF intervals out of the most recent 40 RRIs, the threshold number of NSR beats may be set relatively high, e.g., 4 out of 8. When the VF NID is set relatively lower, e.g., 18 VF intervals out of 24 RRIs, the threshold number of NSR beats may be set relatively lower, e.g., 2 NSR beat detections out of 6 segments analyzed.

In some examples, in addition to setting the NSR reset threshold number of NSR beat detections required to reset or adjust a tachyarrhythmia interval counter, control circuit 80 may set criteria for detecting each NSR beat at block 520 based on the NSR reset threshold. For example, when the NSR reset threshold is relatively low (e.g., three NSR beats or less), a morphology matching score threshold and/or specific beat feature thresholds for detecting an NSR beat may be set relatively higher or more stringent as described above. A higher morphology matching score (e.g., greater than 70), smaller difference threshold from reference beat features (e.g., within 20% of reference beat features), and all three specific beat features within a respective different threshold from the reference NSR R-wave features may be required to detect an NSR beat when relatively fewer NSR beat detections are required to reset the VT and/or VF interval counters. When a relatively higher number of NSR beat detections are required (e.g., four or more), the morphology criteria may be somewhat less stringent, e.g., a lower morphology matching threshold (e.g., greater than 60), greater difference from specific reference beat feature values (e.g., within 30% of reference beat features), and/or fewer beat features required to match the reference beat features (e.g., only one or two matching beat features). It is recognized that in other examples, block 520 for setting NSR reset criteria is optional, and the NSR reset criteria and NSR beat detection thresholds may be predetermined, fixed values that are not automatically adjustable by control circuit 80.

At block 526, the second cardiac electrical signal segment is analyzed to classify the segment as an NSR beat or a non-NSR beat. The analysis may include interval and/or morphology-based analysis as described above. Interval-based NSR beat detection may be performed at block 526 by detecting an RRI that is equal to or greater than an NSR threshold interval (which may be established as described in conjunction with FIG. 6A). The NSR interval may be required to fall within a regularity difference of the RRI(s) for a predetermined number of preceding detected NSR intervals. In some examples, NSR interval detection criteria may require that a predetermined number of consecutive NSR intervals are detected and are stable (within a variability or difference threshold from one another) before classifying each NSR interval as an NSR beat. When interval-based criteria are met for the currently sensed R-wave, the NSR beat classification buffer may be updated to provide an updated count of NSR beats out of Y consecutive sensed R-waves at block 530. In this example that relies only on RRI analysis for detecting NSR beats, analysis of a second cardiac electrical signal segment may be omitted for detecting NSR beats.

Additionally or alternatively, morphological analysis may be applied to a second cardiac electrical signal segment to detect an NSR beat. For example, as described in conjunction with FIGS. 6B and 7, when the RRI of a sensed R-wave is greater than an updated NSR interval threshold, the corresponding second cardiac electrical signal segment may be analyzed to detect an NSR beat morphology associated with the NSR interval. The second cardiac electrical signal analysis may include determining that the signal waveform morphology matches a previously-established NSR R-wave template and/or that specific beat features determined from a relatively short portion of the buffered second cardiac electrical signal segment match reference NSR R-wave morphology features. An NSR beat may be detected at block 526 based only on RRI analysis, only on morphology analysis of the second cardiac electrical signal or a combination of both. The NSR beat classification buffer may be updated, and the NSR beat count may be increased at block 530.

At block 528, gross morphology metrics are determined from the cardiac electrical signal segment for detecting a tachyarrhythmia morphology present in the second cardiac electrical signal segment. The gross morphology metrics may include a gross morphology amplitude metric and a gross morphology signal width metric as described above in conjunction with FIGS. 10 and 11, respectively. When one of the gross morphology amplitude metric or the gross morphology signal width metric is greater than a respective tachyarrhythmia morphology threshold value, the segment may be identified and counted (at block 530) as a tachyarrhythmia morphology signal segment. In some examples, when a segment meets tachyarrhythmia morphology criteria, the segment is classified as a non-NSR beat in the NSR buffer, regardless of whether the NSR beat criteria were met. As such, a segment that meets NSR beat criteria may not be counted as an NSR beat when the same segment meets tachyarrhythmia morphology criteria.

At block 532, control circuit 80 determines if all reset criteria are met. For example, control circuit 80 may verify that at least one of the VT and/or VF interval counters has reached a reset threshold value. The VF counter value may be required to be at least 7 and or the combined VT/VF counter value may be required to be at least 8 when VT detection is enabled, as examples. When the VT and/or VF interval counters are confirmed to have reached at least a reset threshold value, control circuit 80 may apply the NSR reset threshold established at block 520 and verify that the tachyarrhythmia morphology counter is at a value that is less than a withhold reset threshold number. When the number of NSR beat classifications stored in the NSR beat classification buffer reaches the NSR reset threshold, and the number of tachyarrhythmia morphology classifications stored in the tachyarrhythmia morphology classification buffer is less than a withhold reset threshold number, the reset criteria may be satisfied at block 532.

Control circuit 80 may adjust the VT and/or VF (and/or combined VT/VF) interval counters at block 534. As described above, the VT, VF and/or VT/VF combined counters may each be decreased to a predetermined value, decreased by a predetermined decrement (down to a specified minimum), or decreased by a predetermined portion or fraction of the current value of the respective counter. In some examples, the tachyarrhythmia interval counters may each be adjusted to, and not less than, the R-sense confirmation threshold applied to the respective tachyarrhythmia interval counter at block 514. In the example given above, the VF interval counter is adjusted from a current value when reset criteria are met to a value of 2, and the VT interval counter is adjusted from a current value when reset criteria are met to a value of 3. In this way, the R-sense confirmation threshold continues to be satisfied at block 514 enabling the ongoing analysis of buffered second cardiac electrical signal segments for detecting NSR beats.

In other examples, the adjustment at block 534 is based on the current tachyarrhythmia counter value. To illustrate, if the VF interval counter is at 10 or less, it may be reset to a value of 3 at block 534. If the VF interval counter is greater than 10 but less than 20, it may be reset to a value of 8. If the VF interval counter is 20 or more, it may be reset to a value of 12. In the foregoing examples, the tachyarrhythmia interval counters are adjusted according to a predetermined specification that is not necessarily equal to the number of NSR beats detected. In other examples, the adjustment at block 534 may be a decrement of one in response to each NSR beat detected, e.g., with high correlation to the NSR R-wave template wavelet coefficients and specific beat features of the NSR R-wave template, and the R-wave is not confirmed due to noise or oversensing evidence being detected in the second cardiac electrical signal segment at block 516. In this way, the VT and/or VF interval counters may be dynamically adjusted up or down based on the RRI and the detected NSR beats in combination with other R-wave confirmation criteria applied at block 516.

In some examples, control circuit 80 may adjust the NID required to detect VT or VF (block 537) in response to a threshold number of adjustments (block 535) to the tachyarrhythmia interval counters based on NSR beat detections. As determined at block 535, when three, five or other threshold number of adjustments have been made at block 534 to the tachyarrhythmia interval counter(s) based on NSR reset criteria being met, control circuit 80 may increase the NID threshold at block 537 for VT and/or VF detections. For instance, a nominal NID of 30 VF intervals out of 40 RRIs for detecting VF may be increased to an NID of 45 VF intervals out of 60 RRIs when the VF interval counter has been adjusted a threshold number of times, e.g., at least three times, due to NSR reset criteria being met.

After adjusting the tachyarrhythmia interval counter(s) at block 534 (and optionally adjusting the NID at block 537), control circuit 80 may continue the process of checking if the NID is reached at block 536 and if not determining RRIs at block 510. The analysis of the second cardiac electrical signal segments continues to be performed as long as the R-sense confirmation threshold is met at block 514. When reset criteria are unmet at block 532, control circuit 80 may determine if the NID has been reached at block 536, based on the values of the VT and/or VF interval counters.

When the NID required for detecting VT or VF is reached at block 536, the results of the oversensing analysis performed at block 516 may be used in setting a VT/VF detection rejection rule at block 518 in some examples. When noise or oversensing criteria for setting a rejection rule are met (block 518), a VT or VF detection based on the NID threshold being met at block 536 may be withheld at block 542. A VT or VF therapy is withheld at block 542 when the VT/VF detection is withheld. Various examples of VT/VF detection rejection rules that may be applied based on noise and/or oversensing analysis of second cardiac electrical signal segments are described in the above-incorporated U.S. Pat. No. 10,406,373 (Zhang, et al.) and U.S. Pat. No. 9,956,423 (Zhang, et al.).

After withholding VT/VF detection and therapy at block 542, control circuit 80 may determine if termination criteria are met at block 543. Termination of the fast rate of sensed R-waves (that led to the NID being met) may be detected based on a predetermined number of RRIs that are greater than a tachyarrhythmia detection interval or when a mean, median or other metric of RRIs determined over predetermined time interval is greater than a tachyarrhythmia detection interval. For example, when a threshold number of RRIs longer than the VT detection interval (when VT detection is enabled) or longer than the VF detection interval (when VT detection is not enabled) is detected subsequent to the NID being met, termination may be detected at block 543. In one example, termination is detected at block 543 when at least eight consecutive long RRIs, e.g., greater than the VT detection interval, are detected. In another example, control circuit 80 may detect termination at block 543 when a predetermined time interval elapses and a median RRI is greater than the VT detection interval. For instance, when the median RRI of the most recent 12 RRIs is always greater than the VT detection interval for at least 20 seconds, or other predetermined time period, control circuit 80 may detect termination at block 543. Control circuit 80 may reset the VT and VF interval counters to zero values and return to block 510 in response to detecting termination.

If the NID is reached (block 536), and no VT/VF rejection rules are satisfied at block 518, control circuit 80 may detect the VT/VF episode at block 544. It is to be understood that while the NID may be reached, other criteria may be required to be satisfied, such as no rejection rules being met at block 518, in order to actually detect VT or VF and initiate a therapy response. In response to the VT/VF detection at block 544, therapy delivery circuit 84 may begin charging capacitors at block 546 for preparing to deliver a CV/DF shock. During charging, control circuit 80 may continue to analyze RRIs and/or second cardiac electrical signal segments for detecting NSR beats in some examples. If a threshold number of NSR beats are detected at block 548, the tachyarrhythmia interval counters may be adjusted at block 534. For example, reset criteria that were not met at block 532 prior to detecting VT or VF at block 544 may be met during capacitor charging at block 548. When the reset criteria are met at block 548 during charging, the tachyarrhythmia interval counters may be adjusted at block 534. Since the NID is no longer met after adjusting tachyarrhythmia interval counters at block 534, therapy delivery circuit 84 cancels the VT/VF therapy, and capacitor charging that was started at block 546 is terminated. In other examples, once the NID is met at block 536 resulting in a VT/VF detection at block 544, and capacitor charging begins at block 546, resetting of the VT/VF interval counters may be withheld (block 548 may be omitted).

When the NID is met at block 536 and NSR beats are not detected during capacitor charging (or NSR reset criteria remain unsatisfied or unchecked), VT or VF therapy is delivered at block 550. It is to be understood that other VT/VF rejection rule criteria may be applied after detecting VT/VF and during charging. For example, various noise rejection criteria, T-wave oversensing rejection criteria, P-wave oversensing rejection criteria, SVT rejection criteria, etc. may be required to remain unmet during charging at block 546 before delivering therapy at block 550.

Methods disclosed herein provide for the detection of an underlying NSR when a fast ventricular rate is being detected, e.g., due to noise or cardiac event oversensing. When a probabilistic counter of tachyarrhythmia intervals is used for detecting VT or VF, without requiring consecutive tachyarrhythmia intervals, intermittent episodes of noise or oversensing, particularly in the presence of R-wave amplitude variability can lead to an NID being reached. NSR beats may be occurring during and/or between the intermittent episodes of noise or oversensing. By identifying NSR beats during counting of tachyarrhythmia intervals according to the techniques disclosed herein, the tachyarrhythmia interval counter(s) can be adjusted to a lower value to decrease the likelihood of a false tachyarrhythmia detection while still allowing tachyarrhythmia to be detected with high sensitivity and specificity. Accordingly, the function of the medical device performing the presently disclosed techniques is improved by the integration of specified methods for detecting NSR beats and prescribed adjustments of a tachyarrhythmia interval counter in response to NSR beat detections because this improvement leads to a reduction in the rate of false tachyarrhythmia detection and unnecessary therapy delivery without reducing the rate of true tachyarrhythmia detection and necessary therapy delivery.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:

a sensing circuit configured to receive at least one cardiac electrical signal;

a control circuit configured to:

detect tachyarrhythmia events from the at least one cardiac electrical signal;

increase a value of a first counter in response to detecting a tachyarrhythmia event;

detect normal sinus rhythm events from the at least one cardiac electrical signal;

increase a value of a second counter in response to detecting a normal sinus rhythm event;

determine that the value of the second counter meets a reset threshold number;

decrease the value of the first counter in response to the second counter meeting the reset threshold number; and detect a tachyarrhythmia in response to at least the value of the first counter reaching a tachyarrhythmia detection threshold; and a therapy delivery circuit configured to deliver a tachyarrhythmia therapy in response to the control circuit detecting the tachyarrhythmia.

2. The medical device of claim 1 wherein:

the sensing circuit is further configured to sense cardiac event signals from the at least one cardiac electrical signal; and the control circuit is further configured to:

determine that, of the detected normal sinus rhythm events, at least the reset threshold number of the detected normal sinus rhythm events are detected within a first number of most recent cardiac event signals sensed by the sensing circuit; and determine that, of at least the reset threshold number of the detected normal sinus rhythm events, at least one normal sinus rhythm event is detected within a second number of most recent cardiac event signals sensed by the sensing circuit, the second number being less than the first number.

3. The medical device of claim 1 wherein:

the sensing circuit is further configured to sense cardiac event signals from the at least one cardiac electrical signal; and the control circuit is further configured to:

determine sensed event intervals from the cardiac event signals; and detect each of the normal sinus rhythm events by determining that a sensed event interval of the determined sensed event intervals meets a long interval threshold.

4. The medical device of claim 3 wherein the control circuit is further configured to determine the long interval threshold based on at least one of the sensed event intervals.

5. The medical device of claim 3 wherein the control circuit is further configured to:

detect each of the tachyarrhythmia events by determining that a sensed event interval of the determined sensed event intervals is less than a tachyarrhythmia detection interval threshold; and determine the long interval threshold based on at least one of:

a) the tachyarrhythmia detection interval threshold; or b) at least one of the sensed event intervals that is greater than the tachyarrhythmia detection interval threshold.

6. The medical device of claim 1 wherein the control circuit is further configured to detect each of the normal sinus rhythm events by detecting a normal sinus rhythm morphology from the at least one cardiac electrical signal.

7. The medical device of claim 1 wherein the control circuit is further configured to:

establish an R-wave template from the at least one cardiac electrical signal;

determine one or more R-wave template features from the established R-wave template;

detect each of the normal sinus rhythm events by:

determining one or more features from the at least one cardiac electrical signal; and determining that the one or more features determined from the at least one cardiac electrical signal match the R-wave template features.

8. The medical device of claim 1 wherein the control circuit is further configured to detect each of the normal sinus rhythm events by determining from the at least one cardiac electrical signal at least one of:

a peak polarity;

a signal width; or a peak time interval from a reference time point to a maximum peak amplitude.

9. The medical device of claim 1 wherein the control circuit is further configured to:

detect a tachyarrhythmia morphology from the at least one cardiac electrical signal;

determine that a number of tachyarrhythmia morphology detections is less than a second threshold number; and decrease the value of the first counter in response to the second counter meeting the reset threshold number and the number of tachyarrhythmia morphology detections being less than the second threshold number.

10. The medical device of claim 1 wherein the control circuit is further configured to decrease the value of the first counter to a non-zero value.

11. The medical device of claim 1 wherein the control circuit is further configured to:

determine that the value of the first counter meets a first threshold number; and decrease the value of the first counter in response to the second counter meeting the reset threshold number and the first counter meeting the first threshold number.

12. A method comprising:

sensing at least one cardiac electrical signal;

detecting tachyarrhythmia events from the at least one cardiac electrical signal;

increasing a value of a first counter in response to detecting a tachyarrhythmia event;

detecting normal sinus rhythm events from the at least one cardiac electrical signal;

increasing a value of a second counter in response to detecting a normal sinus rhythm event;

determining that the value of the second counter meets a reset threshold number;

decreasing the value of the first counter in response to the second counter meeting the reset threshold number;

detecting a tachyarrhythmia in response to at least the value of the first counter reaching a tachyarrhythmia detection threshold; and delivering a tachyarrhythmia therapy in response to detecting the tachyarrhythmia.

13. The method of claim 12 further comprising:

sensing cardiac event signals from the at least one cardiac electrical signal;

determining that, of the detected normal sinus rhythm events, at least the reset threshold number of the detected normal sinus rhythm events are detected within a first number of most recent sensed cardiac event signals; and determining that, of at least the reset threshold number of the detected normal sinus rhythm events, at least one normal sinus rhythm event is detected within a second number of the most recent sensed cardiac event signals, the second number being less than the first number.

14. The method of claim 12 further comprising:

sensing cardiac event signals from the at least one cardiac electrical signal; and determining sensed event intervals from the cardiac event signals; and detecting each of the normal sinus rhythm events by determining that a sensed event interval of the determined sensed event intervals meets a long interval threshold.

15. The method of claim 14 further comprising determining the long interval threshold based on at least one of the sensed event intervals.

16. The method of claim 14 further comprising:

detecting each of the tachyarrhythmia events by determining that a sensed event interval of the determined sensed event intervals is less than a tachyarrhythmia detection interval threshold; and determining the long interval threshold based on at least one of:

a) the tachyarrhythmia detection interval threshold; or b) at least one of the sensed event intervals that is greater than the tachyarrhythmia detection interval threshold.

17. The method of claim 12 further comprising detecting each of the normal sinus rhythm events by detecting a normal sinus rhythm morphology from the at least one cardiac electrical signal.

18. The method of claim 12 further comprising:

establishing an R-wave template from the at least one cardiac electrical signal;

determining one or more R-wave template features from the established R-wave template; and detecting each of the normal sinus rhythm events by:

determining one or more features from the at least one cardiac electrical signal; and determining that the one or more features determined from the at least one cardiac electrical signal match the R-wave template features.

19. The method of claim 12 wherein detecting each of the normal sinus rhythm events comprises determining from the at least one cardiac electrical signal at least one of:

a peak polarity;

a signal width; or a peak time interval from a reference time point to a maximum peak amplitude.

20. The method of claim 12 further comprising:

detecting a tachyarrhythmia morphology from the at least one cardiac electrical signal;

determining that a number of tachyarrhythmia morphology detections is less than a second threshold number; and decreasing the value of the first counter in response to the second counter meeting the reset threshold number and the number tachyarrhythmia morphology detections being less than the second threshold number.

21. The method of claim 12 further comprising:

determining that the value of the first counter meets a first threshold number; and decreasing the value of the first counter in response to the second counter meeting the reset threshold number and the first counter meeting the first threshold number.

22. A non-transitory computer readable medium storing a set of instructions that, when executed by a control circuit of a medical device, cause the medical device to:

sense at least one cardiac electrical signal;

detect tachyarrhythmia events from the at least one cardiac electrical signal;

increase a value of a first counter in response to detecting a tachyarrhythmia event;

detect normal sinus rhythm events from the at least one cardiac electrical signal;

increase a value of a second counter in response to detecting a normal sinus rhythm event;

determine that the value of the second counter meets a reset threshold number;

decrease the value of the first counter in response to the second counter meeting the reset threshold number;

detect a tachyarrhythmia in response to at least the value of the first counter reaching a tachyarrhythmia detection threshold; and deliver a tachyarrhythmia therapy in response to detecting the tachyarrhythmia.

* * * * *